(12) United States Patent
Chang

(10) Patent No.: US 7,033,823 B2
(45) Date of Patent: Apr. 25, 2006

(54) CELL-CULTIVATING DEVICE

(75) Inventor: King-Ming Chang, Hsin-Chu (TW)

(73) Assignee: Cesco Bioengineering, Inc., Taichung (TW)

( * ) Notice: Subject to any disclaimer, the term of this patent is extended or adjusted under 35 U.S.C. 154(b) by 548 days.

(21) Appl. No.: 10/245,254

(22) Filed: Sep. 16, 2002

(65) Prior Publication Data

US 2003/0143727 A1    Jul. 31, 2003

Related U.S. Application Data

(60) Provisional application No. 60/352,542, filed on Jan. 31, 2002.

(51) Int. Cl.
*C12M 3/00* (2006.01)
(52) U.S. Cl. ............................. 435/297.2; 435/297.1; 435/286.5; 435/294.1
(58) Field of Classification Search ............ 435/289.1, 435/294.1, 297.1, 297.2, 297.5, 304.2; 92/34, 92/47, 80–83; 417/95
See application file for complete search history.

(56) References Cited

U.S. PATENT DOCUMENTS

| | | | |
|---|---|---|---|
| 4,334,028 A | 6/1982 | Carver | |
| 4,851,351 A | 7/1989 | Akamine | |
| 4,962,033 A | 10/1990 | Serkes et al. | |
| 5,010,013 A | 4/1991 | Serkes et al. | |
| 5,114,855 A | 5/1992 | Hu et al. | |
| 5,153,131 A | 10/1992 | Wolf et al. | |
| 5,223,428 A | * 6/1993 | Rose ...................... | 435/69.1 |
| 5,398,837 A | 3/1995 | Degrassi | |
| 5,449,617 A | 9/1995 | Falkenberg et al. | |

(Continued)

FOREIGN PATENT DOCUMENTS

GB    2314343    12/1997

(Continued)

OTHER PUBLICATIONS

Etienne, E., et al., *Temporary Immersion for Plant Tissue Culture*. In: Altman, A., et al., eds., Plant Biotechnology and In Vitro Biology in the 21st Centruy, Norwell, MA; Kluwer Academic Publishers, 1999; 629-632.

(Continued)

*Primary Examiner*—Leon B. Lankford, Jr.
*Assistant Examiner*—Allison M. Ford
(74) *Attorney, Agent, or Firm*—Birch, Stewart, Kolasch & Birch, LLP

(57) ABSTRACT

The present invention claims and discloses a novel apparatus and method for efficiently cultivating cells with minimal mortality in order to harvest a maximum amount of cellular products generated by the cultivated cells. More particularly, the present invention teaches a method and a device for plating cells and causing maximum adherence of cells of interest. Furthermore, the present invention also teaches a growth substrate means that is capable of providing the largest surface area for cell adhesion and functions as an oxygenator, a depth filter and a static mixer to maximize the production of cellular products by intermittently and periodically provide sufficient oxygen and nutrients to the cells without causing cell death. The device of the present invention is economical and can be disposable thus eliminating complications caused by sterlization and is capable of periodically and intermittently provide oxygen and nutrients to cells, through controlling the amount of culture medium that comes into contact with the growth substrate means.

15 Claims, 34 Drawing Sheets

U.S. PATENT DOCUMENTS

| | | | |
|---|---|---|---|
| 5,527,705 | A | 6/1996 | Mussi et al. |
| 5,702,941 | A | 12/1997 | Schwarz |
| 5,766,949 | A | 6/1998 | Liau et al. |
| 6,001,643 | A | 12/1999 | Spaulding |
| 6,323,022 | B1 | 11/2001 | Chang et al. |

FOREIGN PATENT DOCUMENTS

| | | |
|---|---|---|
| JP | 4-158781 | 6/1992 |
| JP | 10-191961 | 7/1998 |
| WO | 96/25484 | 8/1996 |

OTHER PUBLICATIONS

Varani, J., et al, *Human Diploid Fibroblast Growth in Polystyrene Microcarriers in Aggregate, Cytotechnology*, 22:111-117 (1996).

\* cited by examiner

CELL-CULTIVATING DEVICE

RELATED APPLICATIONS/PATENTS & INCORPORATION BY REFERENCE

This application claims priority to provisional application Ser. No. 60/352,542 filed Jan. 31, 2002 entitled "Cell-Cultivating Device" incorporated herein by reference, together with any documents therein cited and any documents cited or referenced in their cited documents. Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference. More generally, documents or references are cited in this text, and, each of these documents or references ("herein-cited references"), as well as each document or reference cited in each of the herein-cited references (including any manufacturer's specifications, instructions, etc.), is hereby expressly incorporated herein by reference. Reference is also made to U.S. application Ser. No. 09/346,101 filed Jul. 1, 1999, now U.S. Pat. No. 6,323,022B1, each of which is hereby incorporated herein by reference.

FIELD OF THE INVENTION

One of the greatest obstacles in microorganism, cell and/or tissue culturing is that the apparatuses and/or devices employed are bulky, expensive, non-disposable, difficult to sterilize and maintain sterilization and thus increase the chance for contamination and are unable to nourish the microorganisms, cells and/or tissues without injuring the microorganisms, cells and/or even causes cell death. The present invention teaches generally, to culture any microorganisms and cells in vitro and harvest any products produced by any microorganisms and/or cellular products. More specifically, the instant invention claims and discloses a novel apparatus and/or device and method for efficiently maximizing the production of any products produced by the microorganism and/or cellular products, such as protein, and harvesting the same.

BACKGROUND OF THE INVENTION

Large-scale cell culture processes have been developed extensively over the years for the growth of bacteria, yeast and molds, all of which typically possess robust cell walls and/or extra cellular materials thus, are more resilient. The structural resilience of these microbial cells is a key factor contributing to the rapidity of the development of highly-efficient cell culture processes for these types of cells. For example, bacterial cells can be grown in very large volumes of liquid medium using vigorous agitation, culture stirring and gas sparging techniques to achieve good aeration during growth, all the while maintaining viable cultures. Alternatively, bacteria can be grown as a biofilm, however, a growing surface would be required.

In contrast, the techniques to culture cells such as eukaryotic cells, animal cells, mammalian cells and/or tissue are more difficult and complex since these cells are more delicate than microbial cells and have nutrient and oxygen requirements during growth which are more complex and difficult to maintain. Further, animal cells and/or mammalian cells cannot withstand the excessive turbulence and/or shear forces that can be created by an influx of air or gaseous mixtures, such as a mixture containing oxygen, nitrogen and carbon dioxide, that are tolerated more easily by microbial cells. In addition, no animal cells can be directly exposed to gases. Most of the animal cells can only utilize dissolved oxygen in the culture medium. Animal cells and mammalian cells are more likely to be damaged by air and gas influx than are microbial cells and thus, result in increased cell mortality. Bioreactors for larger-scale culturing often have internal moving parts, such as an impeller, which subject the cells to a very high fluid shearing force causing cell damage, sometimes cell death, thus leading to low viability of cultures and as a result reduces protein and/or cell by-product production. Likewise, bioreactors that utilize other types of mechanical parts, harsh air movement, or abrupt fluid movement as a mechanism to achieve cell suspension and/or proper aeration will likely cause damage to cells and hinder cell and tissue growth, which further leads to a decrease in cell by-product production, such a protein.

A primary function of a bioreactor is for research wherein large numbers of cells are grown to refine the minute quantities of an active material, including but not limited to a protein or antibody that are secreted by cells into the growth medium. Another function of a bioreactor is the scale-up laboratory cell culture processes for commercial purposes to mass produce the active proteins made by cells and/or tissues. Because of the need to culture eukaryotic cells and/or prokaryotic cells and/or animal cells and/or mammalian cells in the laboratory in large quantities, bioreactors and culturing devices have become an important tool in research and in the production of cells for producing active proteins and/or antibodies and/or any cell by-products.

Many methods are known in the art for growing cells in culture, both on large and small scales. For smaller-scale cell culturing, many vessels have been developed over the years. Culture dishes, for example, represent one type of culturing vessel. Culture dishes typically consist of a bottom dish, which contains the growth medium, and a removable cover. Although the removable cover provides a convenient access to the culture, cells are often and easily contaminated by microorganisms as a result of repeatingly removing the cover during the culturing process. In fact, contamination is one of the principal challenges to successful cell and tissue culturing techniques.

To overcome contamination with culture dishes, culture flasks were developed. Culture flasks typically have a culture chamber, a small tubular opening located at one end of the flask and a corresponding closure. This design attempts to minimize the exposure of cells to dust, bacteria, yeast and other contaminants. For example, patents teaching culture flasks can be found in U.S. Pat. No. 4,334,028 to Carver and U.S. Pat. No. 4,851,351 to Akamine and U.S. Pat. No. 5,398,837 to Degrassi. Although culture flasks were an improvement over culture dishes, they did not fully remedy the contamination problem. In addition, neither the culture dish nor the culture flask can provide appropriate aeration to cells. Furthermore, the growth surface area available in culture flasks is not adequate, as in culture dishes, thus, placing limits on scaling-up the culturing process using this technology.

Another technology developed for use in cell and tissue culturing were roller bottles. The roller bottle has been widely-used in the art for many years. Although they offer some advantages over dishes and flasks, such as a larger surface area for cell attachment and growth, they are still unable to remedy all of the deficiencies and particularly with scaling up. Collectively, these weaknesses include but are not limited to the large uncontrollable hydrodynamic shear forces associated with a gas headspace and the abundance of turbulent eddies. As a result of the high shear force environment inherent in roller bottles, tissue culturing of larger three-dimensional structures is virtually impossible. Only those cell types that are not damaged by the shear forces and/or are capable of remaining adhered to the wall of the roller bottles can be maintained in culture for an extended period of time. Therefore, long-term maintenance of established cell lines can prove to be difficult with roller bottles due to the constant challenge of the high shear force environment and possible contamination. Examples of patents directed to roller bottles include U.S. Pat. No. 5,527,705 to Mussi et al. and U.S. Pat. No. 4,962,033 to Serkes.

Moreover, although the surface area of roller bottles is greater by comparison to culture flasks and dishes, it is often not considered adequate since the surface for cell adhesion is not necessarily more favorable than the culture flasks and dishes, particularly for scaling up the growth of cell cultures. Some efforts have been made to improve upon the roller bottle by providing a greater amount of surface area per roller bottle. For example, U.S. Pat. No. 5,010,013 to Serkes describes a roller bottle with increased surface area for cell attachment. Serkes relates to the use of corrugated channels added to the interior surface area of the roller bottle to increase capacity for cellular attachment. However, a typical roller bottle provides only a surface area of about 850–1700 $cm^2$ for cultivating cells, a multitude of roller bottles are still required for scaling up production. Although, automation of culturing with a large plurality of roller bottles can save on time and labor investment, these operations are typically costly and limiting.

In addition to the problems of hydrodynamic shear forces and surface-area limitations, a central problem inherent in cell and tissue culturing techniques is attaining and maintaining sufficient oxygenation in the growing culture. It is well-known in the art that prokaryotic cells, eukaryotic cells, including animal cells, mammalian cells, insect cells, yeast and molds all have one major rate-limiting step, oxygen mass transfer.

Oxygen metabolism is essential for metabolic function of most prokaryotic cells and eukaryotic cells with the exception of some fermentative-type metabolisms of various eukaryotic microorganisms, such as yeast. Particularly, with mammalian and animal cell culturing techniques, oxygen flux is especially important during the early stages of rapid cell division. Oxygen utilization per cell is greatest when cells are suspended; requirements for oxygen decrease as the cells aggregate and differentiate. Some mammalian and animal cells are anchorage-dependent, requiring a surface to grow, whereas other mammalian and animal cells are anchorage independent and can be grown in liquid environments regardless of the types of cells. However, these cells all require dissolved oxygen in the medium. Nevertheless, during the later phases of cell culture with both anchorage-dependent and independent cells, as the number of cells per unit volume increases, the bulk oxygen mass transfer requirements once again increases.

Traditionally, at least with anchorage-independent cells, increased requirements for oxygen are accommodated by mechanical stirring methods and the sparging of gases into the culture. However, as discussed, both stirring and the sparging of gases can result in damaging cells, thereby decreasing the viability of the culture and the overall efficiency and productivity of the cell and/or tissue culture. Further, direct sparging of cell and tissue cultures with gas can lead to foam production which, is also detrimental to cell viability.

Some attempts have been made in the art to solve the oxygenation problem during cell culturing. For example, U.S. Pat. No. 5,153,131, issued to Wolf et al. ("Wolf"), relates to a bioreactor vessel without mixing blades. Instead, air travels through an air inlet passageway through a support plate member across a screen and through a flat disk permeable membrane wedged between the two sides of the vessel housing. The oxygen then diffuses across the membrane into the culture chamber due to the concentration gradient between the two sides of the housing.

The Wolf bioreactor, however, presents many disadvantages. Particularly, the rate at which oxygen can diffuse across the disk-shaped membrane is a significant limitation that restricts the size of the culture chamber. Another disadvantage of the flat disk membrane is that it is designed to flex in order to cause mixing within the culture chamber which can result in cell death. The mixing effect is a feature described as being critical for the distribution of air throughout the culture media, however, it will also tend to create shear forces within the chamber, again can be detrimental to cells, consequently providing sufficient gas exchange to sustain the growth of larger cellular structures is a significant and realistic restriction when designing a bioreactor or culture vessel.

An example showing an attempt to overcome the deficiencies thus far described is to make reactors from gas permeable materials. For instance, U.S. Pat. No. 5,702,941, issued to Schwarz et al. ("Schwarz"), entitled "Gas Permeable Bioreactor And Method Of Use" relates to a vessel that is horizontally rotated and the vessel is at least partially composed of gas permeable materials. The gas exchange with the culture medium is intended to occur directly through the gas permeable materials of which the vessel walls are composed.

However, Schwarz discloses that the range of sizes for the vessel is still limited since gas exchange is dependent on the quantity of gas permeable surface area. Schwarz emphasized that as the surface area of the vessel increases, the volume and the amount of culture medium also increases. As such, the preferred dimensions of the vessel described in Schwarz are limited to between one and six inches in diameter while the width is, according to Schwarz, preferably limited to between one-quarter of one inch and one inch. Such size limitations are not suitable for growing three-dimensional cellular aggregates and tissues and/or any scaling up production.

Similarly, U.S. Pat. No. 5,449,617, issued to Falkenberg et al. ("Falkenberg"), entitled "Culture Vessel For Cell Culture" relates to a vessel that is horizontally rotated. The vessel is divided by a dialysis membrane into a cell culturing chamber and a nutrient medium reservoir. Gas permeable materials are used in the vessel walls to enable gas exchange in the cell culturing chamber. However, the vessel is not completely filled with the nutrient medium and a large volume of air is maintained above the fluid medium in both chambers. The Falkenberg vessel, however, is not designed to minimize turbulence within the cell culture chamber but rather, mixing is recited to be an essential step to keep the dialysis membrane wetted. Further, Falkenberg does not contemplate using the vessel to grow cellular aggregates or tissues of any kind.

Others have tried to overcome the oxygenation problem. For example, U.S. Pat. No. 5,766,949, issued to Liau et al.

("Liau"), entitled "Method and Apparatus for Cultivating Anchorage Dependent Monolayer Cells" describes a cell-cultivating system in which the culture medium oscillates up and down with respect to a growth substrate in an attempt to improve the oxygenation of the cells.

Liau, however, presents many disadvantages. One disadvantage of this system is the complexity of Liau's apparatus. The Liau system requires two external storage tanks and a separate growth chamber which holds a series of vertical substrate plates. Multiple peristaltic pumps are required to circulate the growth medium from one storage tank through the culture chamber and then into another storage tank and then back to the first storage tank. Introduction of contaminants is very likely given the complexity and the reliance of the components for the Liau apparatus which are external to the culture chamber, for example, the external tubings, storage tanks, and pumps. Further, sterilization is difficult and laborious due to a relatively large amount of components to the apparatus and the size of apparatus.

Another problem presented by Liau is that the flow of the culture medium through the system would create hydrodynamic shear forces that can easily disrupt and dislodge cells from the substrate plates, thus, reducing the viability of the cells. Furthermore, the vertical substrate plates also discourage cell adhesion since cells that cannot adhere immediately to the plates will simply fall and accumulate at the bottom of the plates and, eventually, most of these cells die. Thus, the culture has a reduced viability, the protein production decreases correspondingly and the system would require continual restarting which is highly inefficient and counterproductive. Moreover, due to the complexity of the system, the harvesting of any secreted protein or cellular product would be cumbersome and time consuming. Lastly, when the growth medium is lowered with respect to the growth substrate plates, the cells become exposed to air, i.e., gaseous environment directly, and thus, may result in cell death. Given the importance of cell and tissue culture technology in biotechnology research, pharmaceutical research, patient care, academic research and in view of the deficiencies, obstacles and limitations exist in the prior art described the present invention overcomes the obstacle and remedies the deficiencies in the prior art by teaching and disclosing a method and an apparatus for cell and tissue culturing that fulfills the long-felt need for a novel method and apparatus to culture cells and tissues that is more reliable, less complex, more efficient, less cumbersome, less expensive, less-labor intensive, capable of increasing cell vitality and producing a higher yield of cellular by-products generated from the cells. The apparatus according to the present invention also reduces contamination, thus increases the longevity of the cell.

SUMMARY OF THE INVENTION

The present invention provides a reliable, simple, inexpensive, possibly disposable and efficient method and apparatus for culturing cells and/or tissues and for harvesting cellular products produced thereof. More specifically, the present invention teaches and discloses a novel method and apparatus for efficiently culture cells of interest such as prokaryotic cells, eukaryotic cells, animal cells, mammalian cells, whereby a continuous supply of both oxygen and nutrients to the cells are provided without directly exposing any cells to gas, thus reduces cell injury and even cell mortality. Moreover, the method and apparatus of the present invention reduce contamination, avoid directly exposing the cells to shear forces caused by gas supply thus, prevent detrimental effects on cells caused by air bubbles and gases. The apparatus according to the present invention can be either automated or manual. Furthermore, the present invention provides a method and apparatus for an easier and more convenient way to produce and harvest secreted cellular products, such as protein, and/or antibiotics, and/or any cellular and/or tissue products from cell or tissue cultures.

The objects of the present invention include but are not limited to: providing a novel method and apparatus for preparing, growing and maintaining cell cultures; providing a novel method and apparatus for growing cell and/or preparing tissue cultures; providing a novel method and apparatus for preparing and growing organ cultures; providing a novel method and apparatus for the culturing of cells in an oxygen and nutrient sufficient environment with minimal contamination; providing a novel method and apparatus for culturing cells with a porous growth substrate that enhances nutrient and oxygen exchange with the cells without directly exposing the cells to air bubbles and/or shear forces caused by an infusion of gases; providing a growth substrate means that maximizes cell adhesion, increased surface area for air-medium contact and functions as a static mixer when the medium in the apparatus of the present invention rises; providing a novel method and apparatus for culturing cells by intermittently submerging and emerging cells in growth medium; providing a method and apparatus for culturing cells with minimal contamination; providing a method and an apparatus for minimizing cell mortality during cell culturing, thereby increasing the production of cellular products; providing a method and apparatus for the culturing cells wherein the hydrodynamic shear forces are greatly reduced or absent entirely to reduce and minimize cell mortality; providing a method and apparatus for culturing cells wherein gas sparging is not necessary to achieve oxygenation of the culture medium; providing a method and apparatus for culturing cells wherein the movement of the growth medium can redistribute dislodged cells and facilitate increased cell adhesion; providing a method and an apparatus to continuously nourish the cells with growth culture medium and oxygenation in order to maximize production of cellular products; providing an increased surface area for cell adhesion; providing a method and apparatus for efficiently preparing and harvesting secreted proteins and other cellular products from cell and/or tissue cultures and providing a method and apparatus for culturing cells wherein the viability of the culture over time is improved.

In one embodiment of the present invention, a cell-cultivating device comprises a first chamber containing a growth substrate means for cell attachment and growth, wherein the growth substrate means is disposed within the first chamber within a gaseous environment. The novel growth substrate means according to the present invention functions as a depth filter to trap and capture cells during cell plating, maximizes surface area for air-medium contact and functions as a static mixer. The device also comprises a second chamber connected to the first chamber optionally through a membrane preferably permeable and more preferably porous, wherein the first chamber can be positioned atop, below and/or side by side and/or in surrounding relationship with the second chamber thus to facilitate culture medium to travel freely between the first and second chambers.

The device of the present invention comprises a driving means for moving the culture media from one chamber to another and vice versa in order to gently redistribute dislodged cells back onto the growth substrate means, thus, maximizing cell adhesion; to mix the culture media thus facilitate air-medium contact; and to ensure equal distribution of nutrients and gases to all cells without injuring or killing the cells.

In a different embodiment of the present invention, a cell-cultivating device comprises a first chamber capable of containing and/or supporting a growth substrate means allows cell attachment and cell growth, wherein the growth substrate means is disposed within the first chamber having a gaseous environment. The device according to the present invention also optionally comprises a second chamber connected to the first chamber and adapted to hold cell culture medium, wherein the second chamber comprises a volume-adjusting and/or volume-regulating means for adjusting the level of the culture medium in the second chamber such that, when the culture medium level of the second chamber is at a minimum level, the cell culture medium is substantially moved into the first chamber and whereas when the culture medium level of the second chamber is at a maximum level, the cell culture medium is substantially returned to the second chamber. The volume-adjusting means can include but not limited to a compressed chamber such as a bellow, a piston, a balloon, a floating bag with an air tube, air pressure and/or any other means that is capable of moving the culture medium from one chamber into another.

The apparatus of the present invention can also comprise a driving means for driving and controlling the fluid and/or liquid volume-adjusting means by further facilitation of the culture medium to move in between the first and second chambers intermittently in order to submerge the growth substrate substantially in the culture medium in order to provide nutrients and dissolved oxygen to cells. Thus, when the culture medium level is at a minimum, the cells on the growth substrate means are exposed to a thin air-growth medium interface in order to receive sufficient oxygenation. When the culture medium volume of the second chamber is maximized the cells are exposed to the nutrients in the culture medium. Exposing the cells to a thin gas-growth medium interface whereby the distance between the cells and the air is separated by a thin film accomplished by regulating the amount of culture medium in the first chamber provides efficient oxygenation to the cells without drying out the cells and subjecting cells directly to the shear force and/or air bubbles created by an infusion of gas, thus causing harm or deleterious effects to the cells.

In yet another embodiment of the present invention, a method for cultivating cells such as prokaryotic cells, eukaryotic cells and/or mammalian cells, the present invention provides a novel method comprising the steps of: providing a first chamber, disposing a growth substrate means to receive cells and encouraging cell adhesion providing a second chamber, connecting the second chamber to the first chamber, providing culture medium in the second chamber, providing a fluid and/or liquid volume-adjusting means optionally in the second chamber in order to move the culture medium from the second chamber into the first chamber and vice versa intermittently to provide sufficient nutrients and oxygen to cells without injuring or killing the cells, redistributing dislodged cells for additional cell adhesion and providing a gas-growth medium interface, and providing a mechanism to replenish fresh culture medium and collecting cellular products in the culture medium. Therefore, the present invention not only provides increased cellular production due to increased cell adhesion, it also provides easy access for harvesting and ensuring minimal contamination of the growing culture since the apparatus of the present invention is and can be pre-sterilized and is disposable, thus prevents problems encountered results in the by re-sterilization of apparatus for reuse. In addition, the present invention provides a novel method to intermittently, but indirectly, nourishes the cells with oxygen through a thin air-growth medium interface thus provides sufficient oxygenation to cells without harming and/or killing the cells.

In still yet another embodiment of the instant invention, the method of the previous embodiment further comprises the step of harvesting the growth medium containing the desired secreted cellular products. This method further comprises the steps of: collecting the growth medium from the cell-cultivating device; harvesting the secreted protein contained in the growth medium; providing and replenishing fresh growth medium into the first chamber of a sufficient amount to support growth of the cell culture; and periodically and intermittently move growth medium from the first chamber to the second chamber and vice versa such that when the level of the culture medium in the second chamber is at a minimum, the growth medium is moved into the first chamber and the growth substrate is substantially submerged in the culture medium and when the level of the culture medium in the second chamber is at a maximum, the growth medium is returned to the second chamber and the growth substrate is substantially exposed to a gaseous environment for oxygenation through an air-growth medium interface. The intermittent, but indirect, exposure of the cells of the growth substrate means to an oxygen-rich environment via a thin gas-growth medium interface and submergence of the cells of the growth substrate means in growth medium provides balanced oxygenation and nutrients to the cells without harming and/or even killing the cells.

These and other embodiments are disclosed or are obvious from and encompassed by the following Detailed Description.

BRIEF DESCRIPTION OF THE DRAWINGS

The following Description, given by way of example, is not intended to limit the invention to any specific embodiments described. The Description may be understood in conjunction with the accompanying Figures, incorporated herein by reference.

FIG. 1A shows when the compressible second chamber is not compressed and the growth substrate means is exposed to a gas-growth medium interface for oxygenation.

Figure 1A:
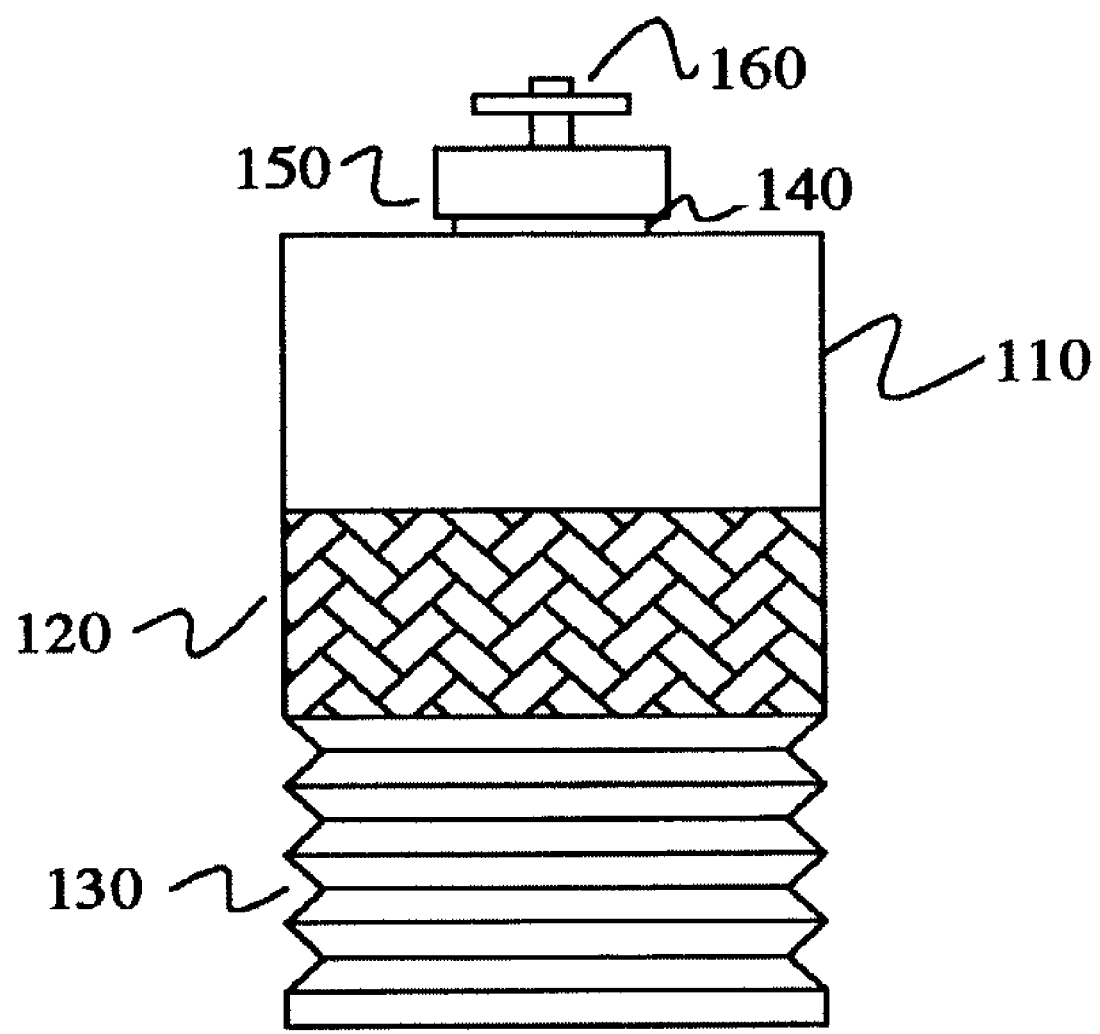
FIG. 1A shows a cell-cultivating device of a first embodiment of the present invention wherein the second chamber is positioned below the first chamber and is optionally compressible to move the growth medium between the first chamber and the second chamber.

These and other embodiment will be described and/or will be obvious from the following detailed description.

DETAILED DESCRIPTION

The following detailed description, given by way of example, is not intended to limit the invention to any specific embodiments described. The detailed description may be understood in conjunction with the accompanying figures, incorporated herein by reference. Without wishing to unnecessarily limit the foregoing, the following shall discuss the invention with respect to certain preferred embodiments. The embodiments of the present invention can be used to culture any cells, such as eukaryotic and prokaryotic cells, particularly animal cells and/or mammalian cells. The present invention inter alia, teaches a cell-cultivating device having at least one chamber and at least one opening and at least one closing means to close the opening. The chamber, for example, can contain, inter alia, cells of desire, growth medium and a growth substrate means to provide a surface area for cell adhesion and growth. In a preferred embodiment, the growth substrate means forms a loosely packed matrix that can function as a depth filter to capture cells during cell plating in order to maximize cell adhesion. The growth substrate means also maximizes air-medium contact by providing a thin air-growth medium interface. The growth substrate means can also function as a static mixer. The growth substrate means is preferably a porous substrate of any size and shape and can be constructed from any material. More particularly, the porous growth substrate means according to the present invention provides a maximum amount of surface area for cell adhesion, growth, gentle stirring, gentle mixing and oxygenation without ever allowing the cells to come into direct contact with air. The chamber system in accordance with the present invention also maximizes cell growth by subjecting cells to a periodic and intermittent exposure of nutrients and oxygen. The system in accordance with the present invention also provides an easy way to collect culture medium containing cellular products as well as replenishing culture medium. The cell-cultivating device of the present invention also protects cells from being directly exposed to any air, gas bubbles or any shear forces generated by an influx of gas, thus, avoiding any detrimental effects to the cells.

More particularly, the present invention is directed to a reliable, simple, inexpensive, disposable, sterile and efficient method and apparatus for culturing cells and/or tissues and harvesting cellular products produced by cells cultured thereof. More specifically, the present invention provides a novel method and apparatus for efficiently culturing any cells whether eukaryotic, prokaryotic, mammalian or animal wherein both oxygen and nutrients needed to ensure cell growth are readily available without causing damage to cells. Furthermore, the method and apparatus of the present invention prevent or greatly reduce the risk of any type of contamination, avoid introducing shear forces on growing cultures, and protect cells from direct exposure to gas, air bubbles and gases. Moreover, the method and apparatus of the instant invention can either be automated or manually carried out with a minimum level of labor involvement and/or supervision. Further still, the instant invention provides a method and apparatus for an easier and more convenient means for producing and harvesting secreted cellular products such as proteins, antibodies from cell or tissue cultures.

In a first embodiment of the present invention, a cell-cultivating device comprises at least one chamber. More particularly, the cell-cultivating device comprises a first chamber capable of containing a growth substrate means for cell adhesion and growth, wherein the growth substrate means is disposed within the first chamber, and it can be intermittently and periodically, but indirectly, exposed to a gaseous environment via a thin gas-growth medium interface in order to receive oxygen or be submerged in culture medium in order to facilitate cell growth and cellular product production. The first chamber also contains at least one membrane, preferably two membranes, the membranes are preferably porous, and more preferably, are permeable, wherein the growth substrate means is disposed between the two membranes to further control and regulate the oxygen and nutrients intake of the cells. This membrane is permeable to the culture medium thus can also serve as a passageway for the culture medium to travel from one chamber to another gently. The device of the instant invention optionally includes a second chamber to serve as a reservoir for culture medium and is connected to the first chamber through the membrane. A portion of the second chamber which acts as a volume-adjusting means, can be compressed and decompressed to move the culture medium from one chamber to another. The first chamber can be optionally positioned atop the second chamber, below the second chamber, side-byside with the second chamber or in surrounding relationship with the second chamber. In addition, the present invention is optionally provided with a driving means to control the volume-adjusting means, hence movement of the culture medium from one chamber to another in order to facilitate a periodic and intermittent submerging of the cells in growth medium in order to provide needed nutrients and emerging from the growth medium in order to indirectly expose cells to a gaseous environment via a thin gas-growth medium interface to provide sufficient oxygenation. The indirect exposure of the cells to the gaseous environment provides sufficient and efficient oxygenation without harming and/or killing the cells.

In another embodiment of the present invention the cell-cultivating device has a first chamber adapted to hold a growth substrate means for cell adhesion and promote cell growth. The growth substrate means is disposed within the first chamber having a gaseous environment and a second chamber matingly connected to the first chamber. A membrane is further disposed between the first chamber and the second chamber. The membrane is preferably substantially porous in order to provide a passageway for culture medium to travel from one chamber to another and the membrane is further adapted to hold the growth substrate means. The second chamber has a volume-adjusting means and/or liquid regulator means for moving the culture medium from one chamber to another. Thus, when the air in the second chamber is minimized, the culture medium substantially remained in the second chamber, whereas when the volume of air in the second chamber is maximized, the cell culture medium is substantially moved into the first chamber. The volume-adjusting means can further be optionally powered by a driving means for regulating, adjusting or controlling the volume-adjusting means in order to move the culture medium from the first chamber to the second chamber and vice versa. Thus, the growth substrate means in the first chamber is periodically and intermittently submerged in the culture medium when the volume for the culture medium in the second chamber is minimized and indirectly exposed to the gaseous environment via a thin gas-growth medium interface to provide adequate oxygenation when the volume of the culture medium in the second chamber is maximized. The indirect exposure of the cells to the gaseous environment via a thin gas-growth-medium interface provides efficient oxygenation of the cells without harming and/or killing the cells since the cells are not in direct contact with air flow.

The first and second chambers of the present invention may be constructed from any material, including but not limited to, polypropylene, plastic or thermoplastic. The volume of each of the chambers can vary and can be of the same or different volume. Preferably, the volume of each chamber ranges from about 10 milliliters to about 5000 milliliters, more preferably from about 50 milliliters to about 2500 milliliters, and most preferably from about 100 milliliters to about 1000 milliliters.

In yet another embodiment, the cell-cultivating device further comprises at least one membrane that divides the first chamber from the second chamber. The membrane can be permeable and can further be porous and adapted to hold and/or support the growth substrate means and functions as a platform.

The permeable membrane can be constructed from any material, for example, including but not limited to semi-permeable fiber, semi-permeable polymer support, or metal or plastic. The permeable membrane can be in any form so long as the membrane can support, hold or sustain the weight of the growth substrate. In a preferred embodiment, the membrane is permeable and porous in order to allow egress and ingress of the culture medium from one chamber to the other without disrupting the cell culture and/or dislodging any cells yet capable of a static mixing. In particular, an additional permeable membrane, that can have the same or similar properties as the first permeable membrane, can be position on an opposite side of the growth substrate means to substantially retain and maintain the growth substrate means in a same position relative to the first chamber as to prevent the growth substrate means from moving during the submergence of the growth substrate means in the growth medium. The growth substrate means in accordance with the present invention can be porous and be made from any material, including but not limited to materials such as ceramics, polymers, woven substrates, non-woven substrates, polyamide, polyester, polyurethane, fluorocarbon polymers, polyethylene, polypropylene or polyvinyl alcohol, glass, silica and DEAE. The porous growth substrate means can be made in any form, shape or size including, but not limited to, a disk, flake, block, plate, sheet, strip, pellet, microcarrier, micropellet, semi-permeable pellet, macroscopic pellet, semi-permeable membrane, or semi-permeable hollow fiber. The utilization of these growth substrate means in accordance with the present invention maximizes surface areas for cell adhesion and air-growth medium surface.

Growth substrate means can also be in a form including but not limited to a hollow fiber, fiber bundle, cell growth cube, and channeled ceramic core. One of the many advantages shared by all of these types of growth substrate means is that the surface area for cell growth and attachment is greatly increased. The growth substrate means of the present invention also contemplates all commercially available substrate systems relating to microcarrier systems, such as hollow fibers, fiber bundles, cell growth cubes, and channeled ceramic cores, as mentioned above. The microcarriers and related substrates contemplated by the instant invention can be coated with proteins and/or other biological or chemical features to enhance the cell adhesion or selectively enhance attachment of particular types of cells.

Microcarrier systems have the potential to facilitate cell growth at commercially advantageous production rates with low labor cost. The cell-cultivating device of the present invention makes both small scale and large scale cell replication and cell production possible as opposed to roller bottles and other known systems. In addition, microcarrier bioreactor systems are well-suited for automated large scale cultivation of anchorage dependent cells.

The use of microcarriers in anchorage-dependent cell production systems requires the availability of a stirring system for oxygenating the cell culture. The system elements interact with one another to maintain the cell-laden microcarrier beads in suspension in the nutrient medium. In contrast, the present invention does not require a stirring system for providing sufficient nutrients and oxygenation to the cells since the intermittent and periodic movement of the culture medium from one chamber to another facilitates mixing and also gives any dislodged cells a second chance to re-attach themselves to the growth substrate means and hence maximizing cell adhesion, ergo, improved cell growth and increased cellular product production.

To be useful as a microcarrier, a material must have a surface chemistry which supports cell attachment and growth, and must not be toxic to the cells or to the elaborated products. The ideal microcarrier should have a diameter of approximately 75–225 µm, although larger or smaller sizes (U.S. Pat. No. 5,114,855 (May 1992); J. Varani, S. Josephs and W. Hillegas, "Human Diploid Fibroblast growth in polystyrene microcarriers in aggregates", Cytotechnology, 22: 111–117 (1996)) have been used.

The present invention teaches a novel growth substrate means in the form of a pellet. The growth substrate means can be of a variety of sizes, having a diameter ranging from about 1 millimeter to about 100 millimeters, although any diameter may be deemed suitable depending on the individual needs. Further, in the instant invention, the pellet can be of any shape or form deemed useful. In a preferred embodiment of the present invention, the growth substrate means is a irregularly-shaped pellet that are loosely packed as a matrix.

The ideal density for the pellet in accordance with the present invention may be in the range of 1.02–1.05 g/cc, although lighter or heavier material may be better suited for different applications. In addition to differences in surface chemistry, pellet made from one substance or another differs in such characteristics as rigidity, porosity and adsorptive capacity. Differences in handling characteristics, durability, shelf-life and ease of sterilization all distinguish one substance from another as does overall manufacturing costs. From the standpoint of commercial potential, the present invention is adaptable to all of these variables.

According to a preferred embodiment of the present invention, a porous growth substrate means and/or pellet is provided. The porous growth substrate means is used to provide enhanced growth and viability of the cells in at least three ways.

First, when the porous pellet is submerged in the growth medium, there can be a gentle stirring occurring in the porous spaces of the pellet, such as with semi-permeable pellet microcarrier less a mixing device. Thus, the porous growth substrate pellet can function as a static mixer, since it creates a gentle stirring environment upon movement of the growth medium. Without being bound by theory, this gentle stirring effect improves the growth of the cells by gently mixing and distributing nutrients and redistributing dislodged cells and increasing the likelihood that the dislodged cells re-adhere and/or re-attach to the growth surfaces. Redistribution of dislodged cells, particularly with anchorage-dependent cells, can help improve overall culture viability.

Second, when the porous pellet growth substrate is not submerged in growth media, the inherent structure of the porous substrate can provide efficient oxygenation to the cells while protecting the cells from being directly exposed to a gaseous environment. Thus, the porous pellet growth substrate functions as an efficient oxygenator of the cells. Direct exposure of cells to a gaseous environment can be detrimental to cell growth and further cause damage or death which is particularly true with animal cells. When the growth substrate means emerges from the culture medium, a portion or coating of growth medium remains on the surfaces of the porous pellet, thereby covering the cells embedded or growing on the substrate means in a thin layer of growth medium. This creates a thin gas-growth medium interface that allows for efficient diffusion of oxygen allowing the cells to efficiently uptake oxygen without directly exposing the cells to air. Furthermore, the porous pellet growth substrate maximizes a surface area for cell growth and for cells to come into contact with an air-growth medium layer.

Third, the porous pellet growth substrate functions as a depth filter to trap cells during plating and/or inoculation thereby increasing the number of adhered cells. The porous pellet growth substrate can form a loosely packed bed which allows for easy and efficient distribution of the cells during inoculation and assures a maximum cell adhesion on the surfaces of the porous pellet growth substrate means.

The air useful for the present invention can be any suitable mixture of gases suitable for any cell growth including but not limited to air. The first chamber of the cell-cultivating device of the instant invention can have at least one opening, wherein the at least one opening is adapted to receive and remove cell culture medium and cells and allows for the exchange of air between the cell-cultivating device and the external environment. The opening is adapted to receive a closing means. Optionally, a filter can be placed between the opening and the closing means to receive air supply and minimize contaminants. The opening can be of any shape or diameter.

The closing means can be of any shape or form including but not limited to a screw cap or a snap cap. Further, the closing means can be constructed from any material including but not limited to plastic. In a preferred embodiment, the closing means may contain an air filter such that the air filter does not allow the passage of microorganisms, cells, viruses or any contaminants into or out from the cell-cultivating device. Sterilizing air filters are known in the art and are commercially available, for example, from Millipore, Mass.

The cells of the present invention can be either eukaryotic cells and/or prokaryotic cells. In a preferred embodiment, the cells are animal cells, mammalian cells, preferably human cells. The cells can be any type of recombinant or non-recombinant prokaryotic cell or eukaryotic cell, including, for example, insect cells, e.g. Sf-9, primate cells, e.g., Vero, mouse, e.g., BHK or C-127, hamster, e.g., CHO, fungal, e.g., *Saccharomyces* or *Scizosaccharomyces,* or human, e.g., tumor, osteoblast and mesenchymal stem cells. The prokaryotic cells can be any aerobic or anaerobic, Gram positive or Gram negative bacteria, or recombinant or non-recombinant, including, but not limited to, *Escherichia coli* and *Bacillus subtilis.* Any cells can be grown in the cell-cultivating device in accordance with the present invention. In particular, cells of choice for the present invention can be anchorage-dependent or anchorage-independent. Anchorage-dependent cells require a surface on which to grow whereas anchorage-independent cells can grow in liquid suspension. All cell types require adequate oxygen, nutrients, and growth factors to grow.

In yet another embodiment, the present invention provides a cell-cultivating device for growing three-dimensional tissue cultures. Culturing tissue for transplantation requires several conditions to be met before the tissue receives Food and Drug Administration (FDA) approval. Those FDA requirement, includes, but are not limited to, functionality that ameliorates the disease consistency and reproducibility for growth of tissue construct; and proven sterility. To achieve in vivo functionality, engineered tissue constructs must be three-dimensional. To be reproducible, the cell culture environment should be regulated to match human physiology. Data from the aseptic monitoring of the growing construct can be used to validate sterility and establish specifications.

Transplantable tissue has three key features: 1) an extra cellular matrix for mechanical stability and scaffolding, 2) cell-to-cell contact to maintain viability and function and 3) a three-dimensional shape to segregate cell subpopulations for growth and proliferation. Standard tissue culture approaches (e.g.; t-flasks, petri dishes, roller bottles and stirred roller bottles) have consistently failed to yield transplantable tissue that directly supplants organ function. Failure is often related to the loss of multi-dimensional cell-tocell contacts and the overgrowth of unwanted cell subpopulation. The present invention overcomes the limitations and deficiencies of the prior art. For example, the roller bottles and stirred reactors of the prior art prevent cells from a sustained three-dimensional growth. In addition, with regard to viral production, the Pfu/cell yield from Roller bottle is 195, from the microcarrier/spinner flask is 109 and from the present invention is 313. A two to three fold increase in production. Shear preselects for only those cell subpopulations that are robust to its damage. The present invention reduces and minimizes and controls the addition of turbulence and concomitant shear and avoids preselection of specific populations of cells.

There are other selection pressures introduced by various technical operations of the prior art that impede normal growth, in addition to those intrinsic to standard cell culture roller bottles. Specifically, those technical operations can be associated with feeding the culture.

There are several deficiencies associated with a roller-bottle or stir-tank bioreactor when culture medium needs to be exchanged, changed or replenished. This is termed "medium exchange mode." Specifically, medium exchange modes' such as a perfusion or fed-batch methods for stir-tank bioreactors using microcarriers to support the growth of the cells may be difficult since it may require additional complicated devices, such as spin filters, inclined separation plates, or alternating tangential flow apparatuses. Moreover, when applying the perfusion mode of medium exchange to known methods and apparatuses can cause the washing-away of adhered cells. The present invention remedies this shortcoming by utilizing perfusion mode designed to create a lower shear stress and reduces cell dislodging.

The volume-adjusting and/or volume regulator means of the instant invention can include but is not limited to a compressible chamber such as a bellow, a floating bag, a piston assembly or a balloon. Additionally, the driving means for this invention to power the compressible chamber can be automated or manual.

The mechanism for the volume-adjusting means and/or volume regulator will now be further explained. The automated driving means contemplated by the instant invention can be controlled by an electronic device such as a computer. The control of the driving means of the instant invention can be controlled by any method of automation known to one of skill in the art, for example, robotics can be used to automate the instance invention.

When the volume-adjusting means is a compressible chamber such as a bellow, the bellow will be compressed or decompressed to adjust the amount of culture medium in the bellow. For example, when the bellow is maximally compressed, the culture medium contained within it is at a minimum. When the bellow is maximally decompressed, the culture medium contained within it is at a maximum. More specifically when the bellow is being compressed, there is a concurrent movement of the culture medium from the compressible chamber into the first chamber where the growth substrate means is located in a manner that does not generate a harmful level of shear forces to the cells of the culture. The culture medium containing chamber may be positioned above, below, side-by-side or in surrounding relationship with the chamber containing the growth substrate means. The compression and decompression of the bellow, hence, the movement of the culture medium from one chamber to another can occur at regular and/or irregular intervals and can be optimized to provide the particular cells of the culture an optimal level of oxygenation. Optimal levels of oxygenation are well-known in the art. For example, it is well-known in the art that an excessively high concentration of oxygen can be detrimental to cell growth, particularly with highly differentiated cells. Likewise, it is also well-known in the art that an excessively low oxygen concentration can also be harmful to cell growth since cells, in particular, animal cell and mammalian cells require oxygen for metabolism and growth.

In a second embodiment of the instant invention, the volume-adjusting and/or volume regulator means is a balloon which is adapted to be inflated or deflated in order to adjust the culture medium volume in the second chamber and to move the culture medium from one chamber to another. Accordingly, when the balloon is maximally inflated, the culture medium in the second chamber is at a minimum. When the balloon is maximally deflated, the culture medium in the second chamber is at a maximum. The balloon contemplated by the instant invention can be constructed from any material, for example, rubber, latex, or any expandable plastic. More particularly, since the balloon is positioned in the culture medium containing chamber, thus when the balloon is inflated, there is a concurrent movement of the culture medium from the culture medium containing chamber into the growth substrate means containing chamber in a manner that does not generate a harmful level of shear forces to the cells of the culture. Alternatively, when the balloon is deflated, there is a concurrent movement of the culture medium from the growth substrate means containing chamber back to the culture medium containing chamber and consequently, the growth substrate means is exposed to a gaseous environment and the cells, since they are embedded in the growth substrate means are covered by a thin gas-growth medium interface to receive oxygen. Accordingly, regardless of the type of the volume adjusting and/or volume regulator means employed with the cell-cultivating device of the present invention, the cell culture of the present invention is intermittently and periodically subjected to either submergence in a culture medium to receive nutrients or indirect exposure to a gaseous environment via a thin gas-liquid interface to receive oxygen. The inflation and deflation of the balloon can occur at a regular and/or irregular interval and can be optimized to provide the particular cells of the culture an optimal level of oxygenation.

In a third embodiment of the present invention, the volume-adjusting means is a piston wherein the movement of the piston concurrently moves the culture medium from one chamber to another. For example, when the piston is maximally pushed, the culture medium in the second chamber is at a maximum volume, and when the piston is maximally withdrawn, culture medium in the second chamber is at a minimum.

In another embodiment, the cell-cultivating device according to the present invention has at least one chamber. The device can optionally contains two chambers, namely, a first chamber and a second chamber. The first chamber may be atop, below, side-by-side or in surrounding relationship with the second chamber and vice versa. The first chamber may be adapted to contain a growth substrate means to facilitate cell adhesion and cell growth, at least one membrane, preferably two membranes that are permeable and porous to facilitate movement of the culture medium and a gaseous environment to provide oxygen to the growth substrate means. The growth substrate means can be optionally fixedly engaged and/or attached and/or suspended to an interior surface of the first chamber. The second chamber can contain culture medium and a mechanism to move the culture medium from the second chamber to the first chamber and vice versa. The moving mechanism of the second chamber can be powered automatically and/or manually at regular or irregular intervals in any time interval in a manner that provides optimal level of oxygenation and nutrients to the cells of the culture. The first chamber is connected to the second chamber via the membrane. In a preferred embodiment, the growth substrate means is disposed between the two porous membranes.

Alternatively, the present invention provides a cell-cultivating device comprising a cell containing growth substrate means disposed in the first chamber and a culture medium containing second chamber both having a first or a distal end and a second and proximal end. The second chamber is adapted to contain culture medium substantially at the distal end and to contain a gaseous environment substantially at the proximal end. The cell culture chamber can be made from any material such as, plastic or polypropylene. The first chamber and the second chamber are matingly fitted or optionally integral with each other.

The fourth embodiment of the present invention comprises an enclosed floating bag and/or a container assembly as a volume adjusting or liquid regulator means fixedly engaged to a surface or membrane that is optionally porous and having a growth substrate means atop, wherein the floating bag utilizes air contained therein to move the growth substrate means in a vertical motion thus concurrently causes the culture medium to move. For example, when the floating bag is inflated with air, the growth substrate means is propelled upwardly moving out of the immersion of the growth substrate medium and indirectly exposed to a gaseous environment via a thin gas-liquid interface to provide oxygenation. When the floating bag is deflated, the growth substrate means is propelled downwardly and submerged in the culture medium for cells to receive nutrients. The floating bag assembly can be made from any suitable material.

The present invention can be optionally provided with a driving means, such as, an air compressor, in order to automatically or manually inflate or deflate the floating bag assembly to facilitate oxygenation and nutrients to cells adhered to the growth substrate means.

A sixth embodiment of the instant invention provides a cell-cultivating device comprising a first chamber having a growth substrate means disposed and suspended therein, the first chamber has a first or a proximal end and a second or a distal end, wherein the distal end of the first chamber is substantially open to a second chamber that is in surrounding relationship with the first chamber. The second chamber, having a first or a proximal end and a second or a distal end, whereby the proximal end is substantially sealed. The growth substrate means is submerged in the culture medium when air is pumped into the second chamber via the proximal end and indirectly exposed to a gaseous environment via a thin gas-growth medium interface when air is withdrawn from the second chamber. Air can be pumped in or withdrawn from the second chamber by any driving means such as an air compressor and the driving means can be powered automatically or manually.

The present invention provides a novel method to culture cells that can be eukaryotic and/or prokaryotic, preferably, animal cells and mammalian cells comprising the steps of: dispensing growth medium and cell suspension onto a growth substrate means disposed within a first chamber of a cell-cultivating device; providing at least one surface and/or a membrane to support the growth substrate means wherein, the membrane and/or the surface is preferably porous; providing at least one opening at a first end of the first chamber to allow the addition and/or removal of growth medium and cells, at least one closing means adapted to seal the opening. The closing means is optionally provided with a filter to allow exchange of air and to minimize contaminants from entering into the chamber. The device is also provided with a second chamber to receive the culture medium, a volume-adjusting means to move culture medium from one chamber to another and a method to harvest cellular products generated by cells that are contained in the culture medium.

The cell-cultivating device of the present invention further comprises at least one membrane barrier that may be permeable and/or porous and is adapted to separate the first chamber from the second chamber. Furthermore, in a preferred embodiment, there is a membrane on either side of the growth substrate means in order to confine the cell-containing pellets. The second chamber can contain culture medium and may be atop and/or below and/or side by side and/or in surrounding relationship with the first chamber thus, allowing the growth medium to gently flow or travel between the first chamber and the second chamber. The membrane can be made from material such as, semi-permeable fiber, semi-permeable polymer support, or metal or plastic. Further, the membrane is capable of supporting or holding and/or confining the growth substrate means in place.

The present invention further comprises the step of inoculating and/or plating the cells on the growth substrate means.

Further, the present invention also provides a novel method of periodically and or intermittently moving the growth substrate means or the culture medium within the cell-cultivating device in order to either submerge cells adhered to the growth substrate means in the culture medium to provide nutrients to the cells or to indirectly expose cells adhered to the growth substrate means to a gaseous environment via a thin gas-growth medium interface for oxygenation of the cells by emerging the growth substrate means out of the culture medium without injuring and/or killing the cells.

Figure 1B:
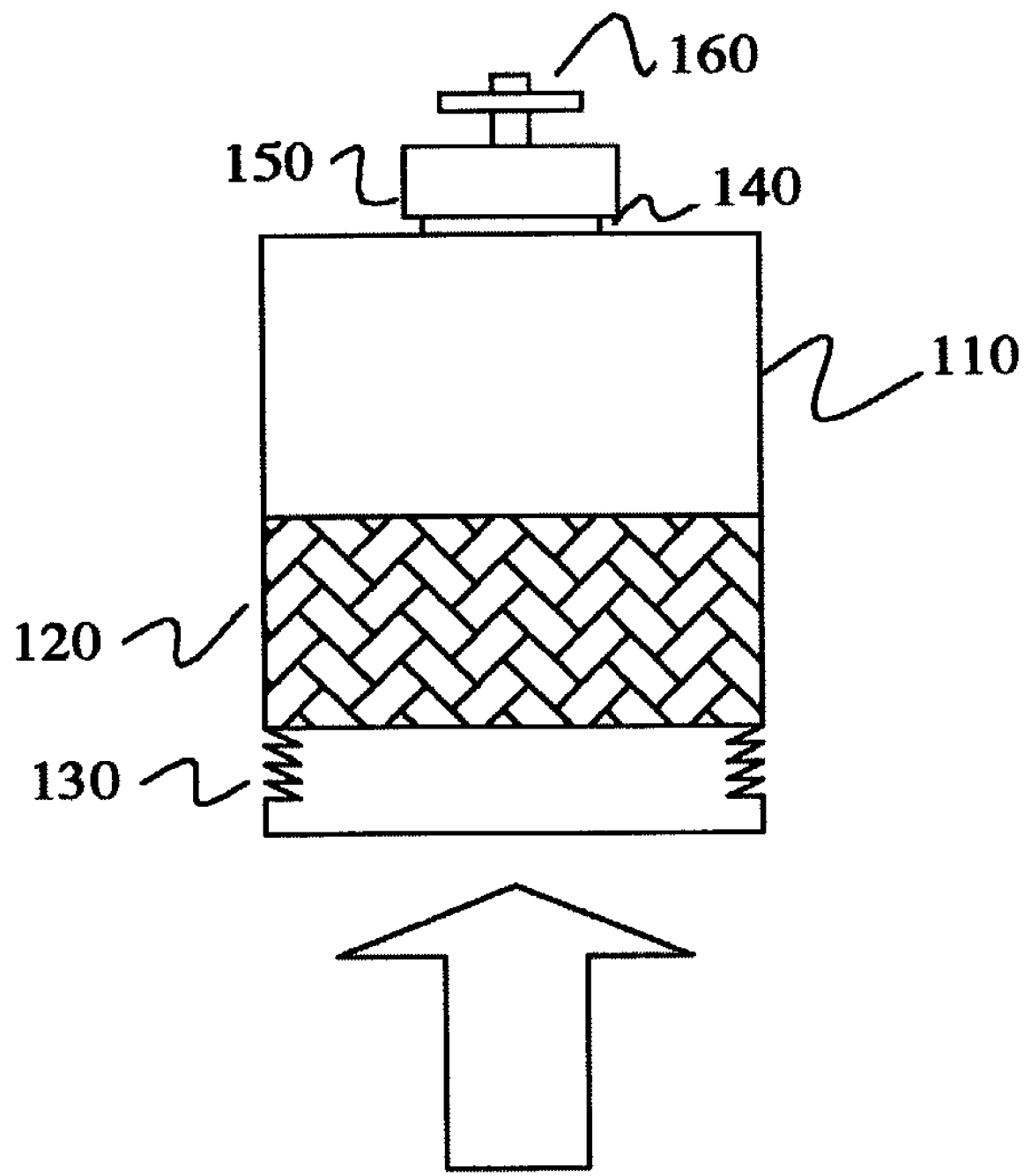
FIG. 1B shows a cell-cultivating device of the first embodiment of the present invention wherein the compressible second chamber is compressed and the growth substrate means is submerged in the growth medium for cells to receive nutrients.

In a further embodiment of the instant invention, the method of the previous embodiment further comprises the step of harvesting the growth medium containing secreted cellular products. The secreted cellular products can include, but are not limited to, protein, DNA, RNA, plasmids, antibodies, and viruses. The step of harvesting the growth medium comprises the additional steps of: collecting the growth medium from the cell-cultivating device through the opening provided in the first chamber by decanting and/or any conventional method and harvesting the secreted protein contained in the growth medium. Any method of harvesting the growth medium known in the art is contemplated by the instant invention, such as, for example, decanting and/or aspiration of the growth medium from the culture chamber. After removal of the spent cell medium, the method of the present invention also provides the steps of: refilling fresh culture medium into the cell-cultivating device of a sufficient volume after the harvesting to nurture and nourish the cell culture. The growth substrate means will once again be submerged in the fresh culture medium periodically and intermittently and cells will be indirectly exposed to a gaseous environment via a thin gas-growth medium interface as the volume of the second chamber goes from minimum to maximum as previously described. Thus, the cell-cultivating device can be carried out perpetually until the cells fail to produce the desired cellular products. Since the cell-cultivating device of the present invention is of a simple construct, therefore it is inexpensive and disposable thus avoid problems associated with sterilization of the equipment Reference is now made to the figures by way of examples and they are by no way limiting the scope of the present invention. FIGS. 1A and 1B depict a cell-cultivating device of the first embodiment of the present invention. A first chamber 110 contains growth substrate means 120. Growth substrate means 120 may be constructed from any suitable material such as, ceramics, polymers, woven substrates, non-woven substrates, polyamide, polyester, polyurethane, fluorocarbon polymers, polyethylene, polypropylene or polyvinyl alcohol, glass, silica and DEAE. The growth substrate means 120 may be optionally porous. The growth substrate means 120 allows for cell adhesion and for the cells contained thereon to be oxygenated without being directly exposed to the gaseous environment. Direct exposure of cells, particularly animal cells and mammalian cells can be harmful and can lead to cell death and loss of viability of the culture.

The growth substrate means 120 can be of any form, shape or size including but not limited to a disk, flake, block, plate, sheet, strip, pellet, microcarrier, semi-permeable pellet, macroscopic pellet, semi-permeable membrane, or semi-permeable hollow fiber.

First chamber 110 is connected to a second chamber 130 and the first chamber 110 is either matingly-fitted with the second chamber 130 or is integral with the second chamber 130, wherein first and/or second chamber may contain growth medium and both chambers have at least one open line of communication to enable fluid and air to flow and travel from one chamber to another. In the first embodiment, the second chamber 130 has a compressible component that may be in the form of a bellow that can be compressed and decompressed. Second chamber 130 may contain growth or culture medium. FIG. 1A shows the compressible component in the second chamber 130 in a non-compressed form, thus, fill the second chamber with culture medium. Consequently, the growth substrate means 120 is indirectly exposed to a gaseous environment via a thin gas-growth medium interface to receive oxygenation. FIG. 1B depicts when the compressible component in the second chamber 130 in a compressed form. When second chamber 130 is in a compressed form, the growth medium is moved into first chamber 110 and the growth substrate means 120 is submerged within the growth medium. Whereas, when second chamber 130 is in a non-compressed form, the growth medium is contained in the second chamber 130 and growth substrate means 120 is not submerged in the growth medium. The first chamber 110 may be provided with at least one opening 140 for loading or withdrawing cells and culture medium into or out of the first chamber 110. Opening 140 is adapted to receive a closing means 150. Closing means 150 comprises at least one air filter 160 to sterilize air passing in or out of the cell-cultivating device in order to minimize contamination.

Figure 2A:
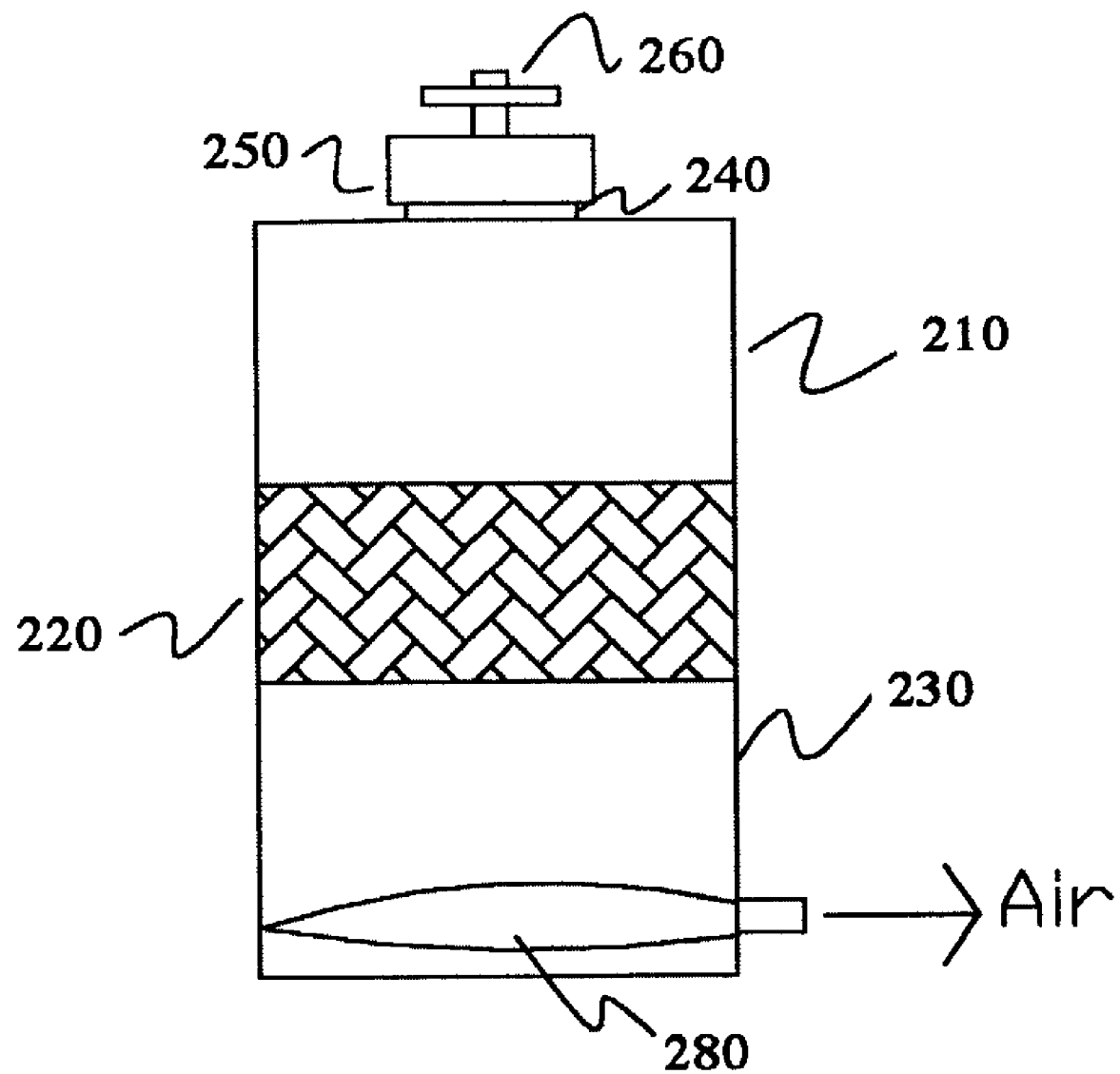
FIG. 2A shows a cell-cultivating device of a second embodiment of the present invention wherein an expandable balloon is placed and/or position in the second chamber and is deflated to cause the growth medium to remain in the second chamber such that the growth substrate means of the first chamber is indirectly exposed to a gaseous environment via a thin gas-growth medium interface.
Figure 2B:
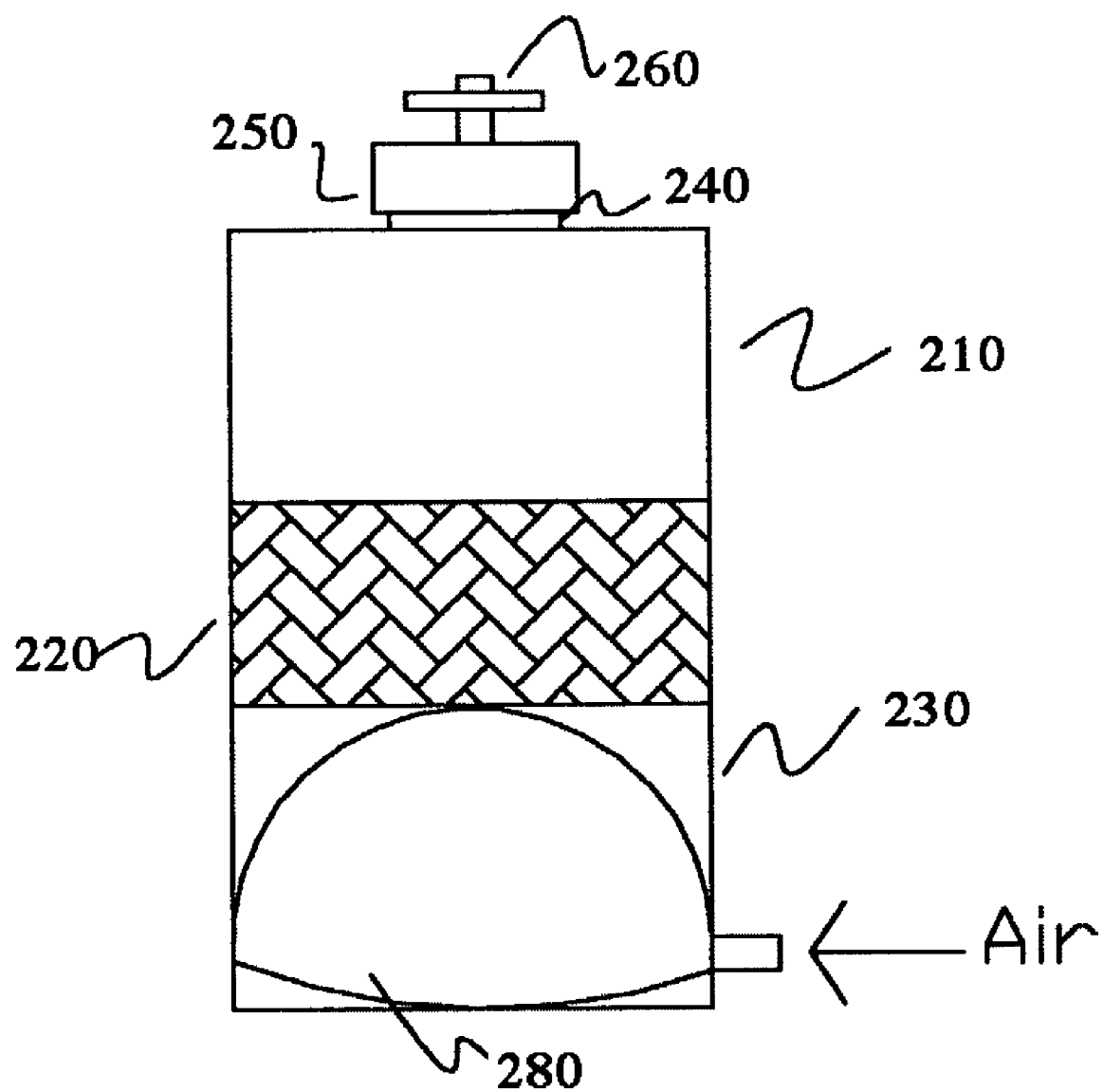
FIG. 2B shows a cell-cultivating device of the second embodiment of the present invention wherein the expandable balloon is inflated thus forcing the growth medium to flow or travel from the second chamber into the first chamber resulting in submerging the growth substrate means and, thus, the cells in the growth medium.

Referring to FIGS. 2A and 2B, a cell-cultivating device of a second embodiment of the present invention is presented. Reference is made to the figures. A first chamber 210 contains growth substrate means 220. Growth substrate means 220 may be formed of a loosely-packed matrix made from material including but not limited to ceramics, polymers, woven substrates, non-woven substrates, polyamide, polyester, polyurethane, fluorocarbon polymers, polyethylene, polypropylene or polyvinyl alcohol, glass, silica and DEAE. In the second embodiment, the growth substrate means 220 may be optionally porous. The growth substrate means 220 allows the cells contained thereon to be oxygenated without being directly exposed to the gaseous environment. Direct exposure of cells, particularly animal cells and/or mammalian cells, can be harmful and can lead to cell death and loss of viability of the culture.

The growth substrate means can be made from any pellets of any form, shape or size including but not limited to a disk, flake, block, plate, sheet, strip, pellet, microcarrier, semi-permeable pellet, macroscopic pellet, semi-permeable membrane, or semi-permeable hollow fiber.

First chamber 210 is connected to second chamber 230, wherein first and/or second chamber may contain growth and/or culture medium and both chambers are substantially open to each other at their interface to facilitate fluid and gas exchanges and movements. In the second embodiment, the second chamber 230 may contain a compressible component in a form of a balloon 280 as a volume-adjusting means. Second chamber 230 may optionally contain growth medium. FIG. 2A shows balloon 280 in a deflated state in the second chamber 230. FIG. 2B depicts balloon 280 in an inflated state in the second chamber 230. Balloon 280 may be constructed of any material such as, for example, rubber, latex, or an elastic polymer.

When balloon 280 is in an inflated state as shown in FIG. 2B, the growth culture medium volume of second chamber 230 is at a minimum and the growth medium is substantially forced into the first chamber 210 causing the submersion of growth substrate 230 in the growth medium. When balloon 280 is in a deflated state as shown in FIG. 2A, the volume for growth culture medium in the second chamber 230 is at a maximum causing the growth substrate 220 to be indirectly exposed to a gaseous environment of first chamber 210 via a thin gas-growth medium interface to receive oxygenation. First chamber 210 may be provided with at least one opening 240 for loading, plating or inoculating or withdrawing cells onto the growth substrate means and culture medium into or out of the first chamber 210 and for exchanging air with an environment external to the first chamber 210. Opening 240 is fitted with a closing means 250. Closing means 250 is further fitted with at least one air filter 260 to sterilize air passing in or out of the cell-cultivating device.

Figure 3A:
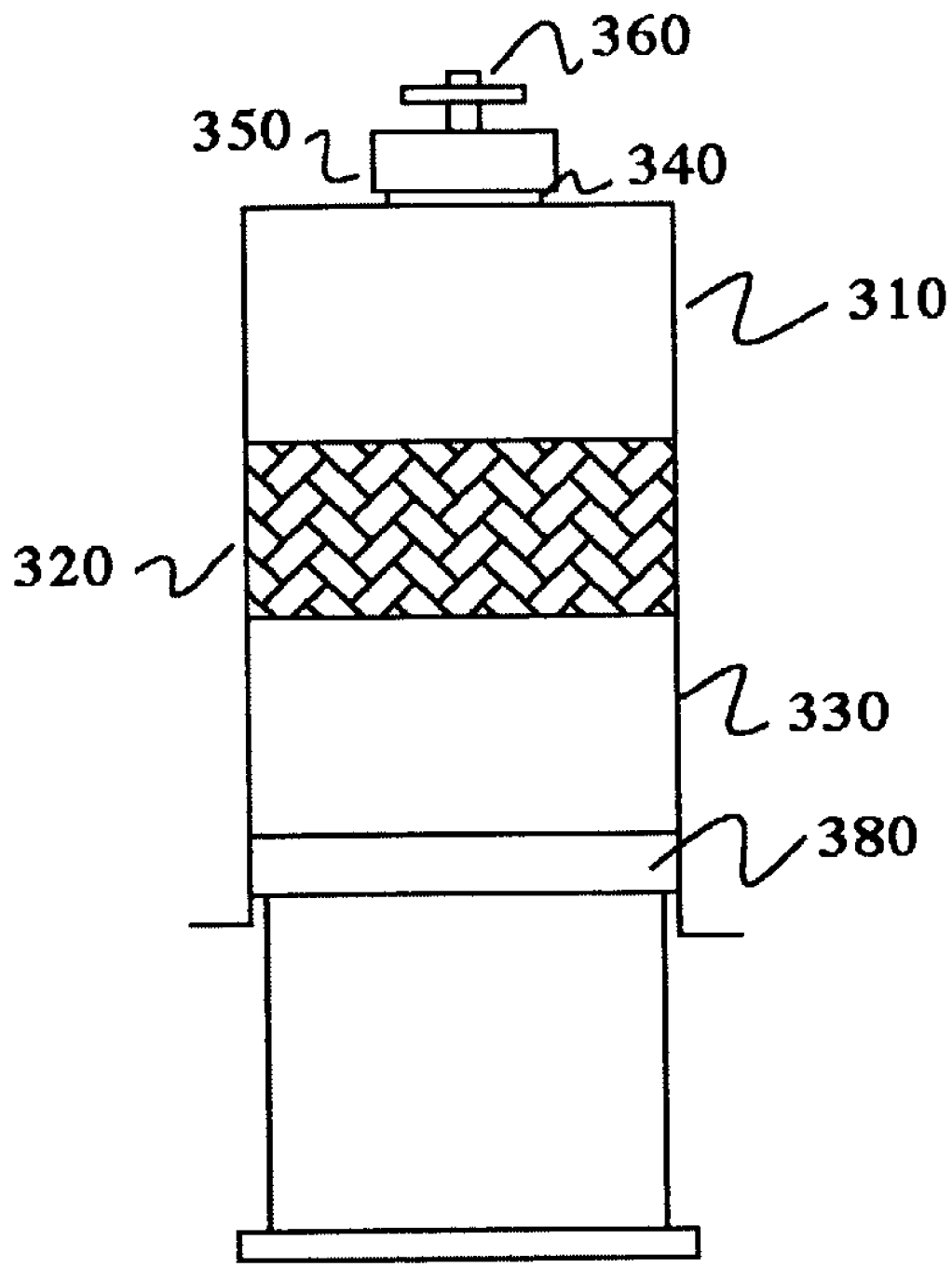
FIG. 3A shows a cell-cultivating device of a third embodiment of the present invention wherein a piston is positioned in the second chamber and is fully drawn and maintaining the growth medium to remain in the second chamber such that the growth substrate means of the first chamber is indirectly exposed to a gaseous environment via thin gas-growth medium interface. Thus, cells are never exposed to gas and/or air directly.
Figure 3B:
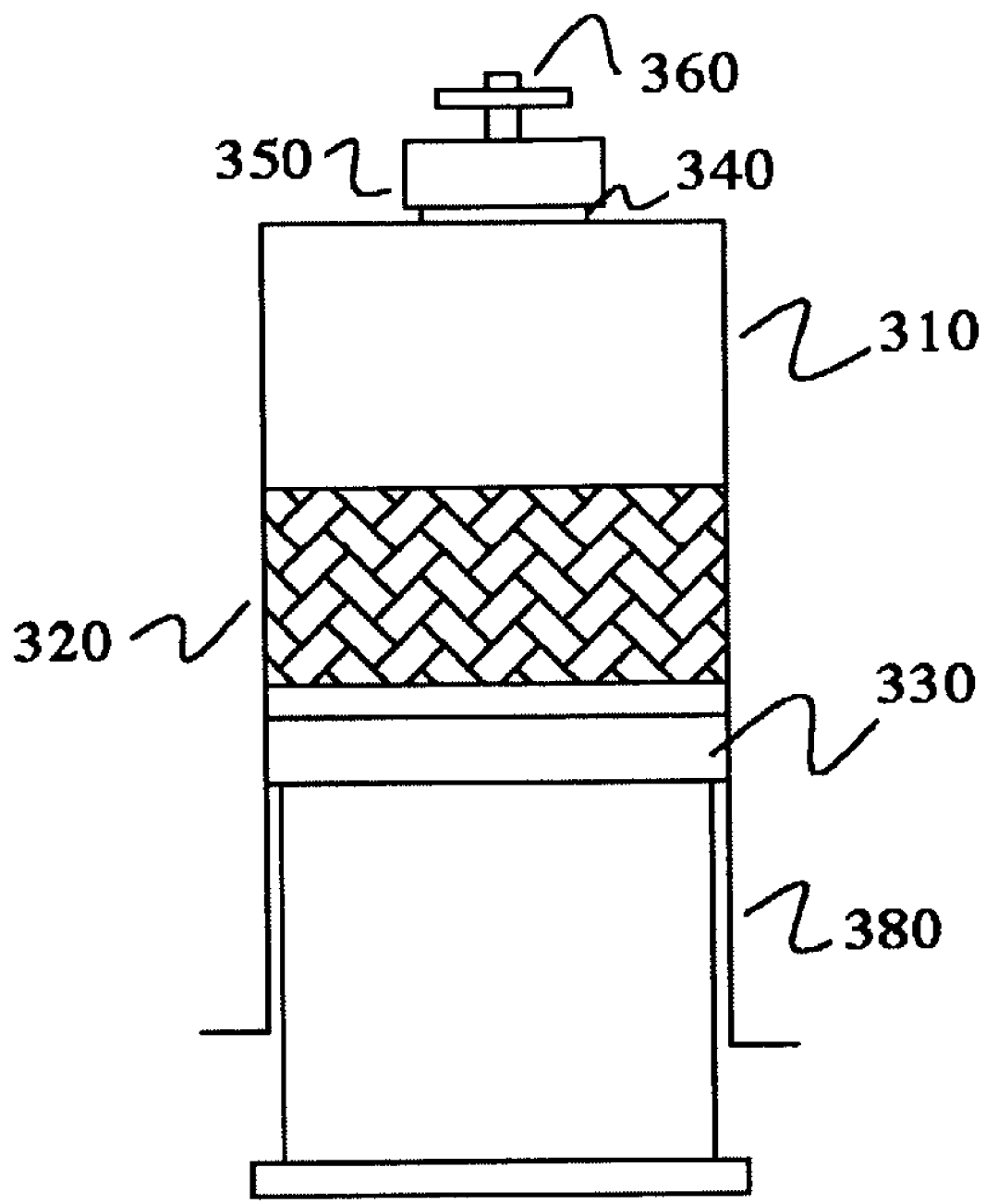
FIG. 3B shows a cell-cultivating device of the third embodiment of the present invention wherein the piston in the second chamber is pushed upwards to force the growth medium to flow or travel or move from the second chamber into the first chamber and submerging the growth substrate means in the growth medium in order to provide nutrients to cells.

Referring to FIGS. 3A and 3B, a cell-cultivating device of a third embodiment of the present invention. A first chamber 310 contains a growth substrate means 320. Growth substrate means 320 may be constructed from any material such as, ceramics, polymers, woven substrates, non-woven substrates, polyamide, polyester, polyurethane, fluorocarbon polymers, polyethylene, polypropylene or polyvinyl alcohol, glass, silica and DEAE. In the third embodiment, the growth substrate means 320 may be optionally porous or may be made from a compilation of pellets in order to form a loosely-packed matrix. The porous growth substrate 320 allows the cells contained thereon to be oxygenated without being directly exposed to the gaseous environment. Direct exposure of cells, particularly animal cells and/or mammalian cells, can be harmful and can lead to cell death and loss of viability of the culture.

The growth substrate means 320 can be of any form, shape or size, such as, disks, flakes, blocks, plates, sheets, strips, pellets, microcarriers, semi-permeable pellets, macroscopic pellets, semi-permeable membranes, or semi-permeable hollow fibers.

First chamber 310 is connected to the second chamber 330, wherein first and/or second chamber may contain growth medium and both chambers are substantially open to each other at their interface. In the third embodiment, the second chamber 330 may comprise a piston 380 as a volume-regulating means. The piston may be pushed upward or pulled downward to concurrently move the culture medium in the second chamber 330 into or out of the first chamber 310 thereby adjusting the volume of the growth medium in the second chamber 330. FIG. 3A shows piston 380 in the pulled downward position, wherein the volume of the growth culture medium in the second chamber 330 is at a maximum. FIG. 3B shows piston 380 in the pushed upward position, wherein the volume of the growth culture medium in the second chamber 330 is at a minimum. Piston 380 may be constructed of any material such as, rubber, plastic, metal, synthetic material or polypropylene and operated in a conventional method.

When piston 380 is in the downward position, growth medium substantially remained in the second chamber 330, thus exposing the growth substrate 330 for oxygenation in the first chamber 310. When piston 380 is in the upward position, the piston drives the growth medium into the first chamber 310 causing the growth substrate 320 to be submerged in the growth culture medium. First chamber 310 may optionally have at least one opening 340 for loading or withdrawing cells and culture medium into or out of first chamber 310 and for exchanging air with the environment external to first chamber 310. Opening 340 is fitted with a closing means 350. The closing means 350 is optionally fitted with at least one filter 360 to sterilize air passing in or out of the cell-cultivating device.

Figure 4:
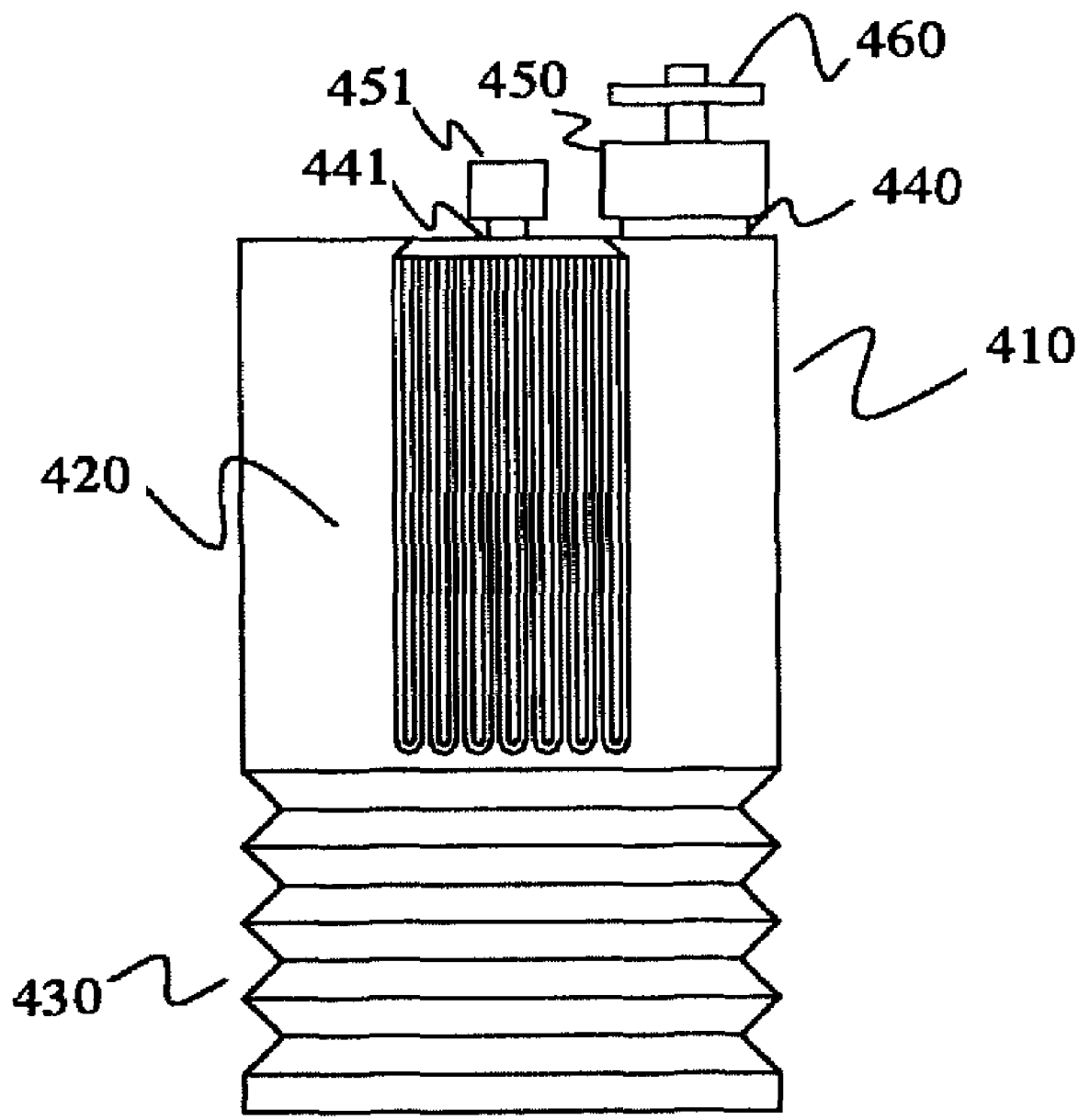
FIG. 4 shows a cell-cultivating device of a fourth embodiment of the present invention whereby the growth substrate means is a hollow fiber.

Reference is made to FIG. 4, a cell-cultivating device of a fourth embodiment of the present invention which has a first chamber 410 containing at least one semi-hollow fiber growth substrate means 420. Semi-hollow fiber growth substrate means 420 may be constructed from any material such as woven substrates, non-woven substrates, polyamide, polyester, polyurethane, fluorocarbon polymers, polyethylene, polypropylene or polyvinyl alcohol, glass, silica and DEAE. Semi-hollow fiber substrate 420 allows the cells contained therein to receive oxygen without being directly exposed to the gaseous environment. Direct exposure of cells to air, particularly animal cells and mammalian cells can be harmful and even lead to cell death and loss of viability of the culture.

First chamber 410 may be integral or matingly-fitted with second chamber 430, wherein first and/or second chamber may contain growth culture media and both chambers are substantially open to each other at their interface. In the current preferred embodiment, second chamber 430 may take the form of a bellow, which may be compressed or decompressed to change the volume of the growth culture medium contained in the second chamber 430 as previously described in FIGS. 1A and 1B.

When second chamber 430 is compressed (not shown), growth culture medium is substantially moved into the first chamber 410 causing the semi-hollow fiber growth substrate 420 to be submerged in the growth medium to nourish the cells. When second chamber 430 is not compressed, the growth media is substantially returned and/or remained in the second chamber 430 thus providing oxygenation cells in or on the semi-hollow fiber growth substrate 420. First chamber 410 may optionally contain at least one opening 441 for loading cells onto semi-hollow fiber substrate 420 and is adapted to receive a closing means 451 for reversibly sealing opening 441. First chamber 410 may also be provided with a second opening 440 for loading or withdrawing culture medium into or out of the first chamber 410 and for exchanging air with the external environment. Opening 440 is reversibly sealed with a second closing means 450. Closing means 450 comprises at least one air filter 460 to sterilize air passing in or out of the cell-cultivating device.

Figure 5:
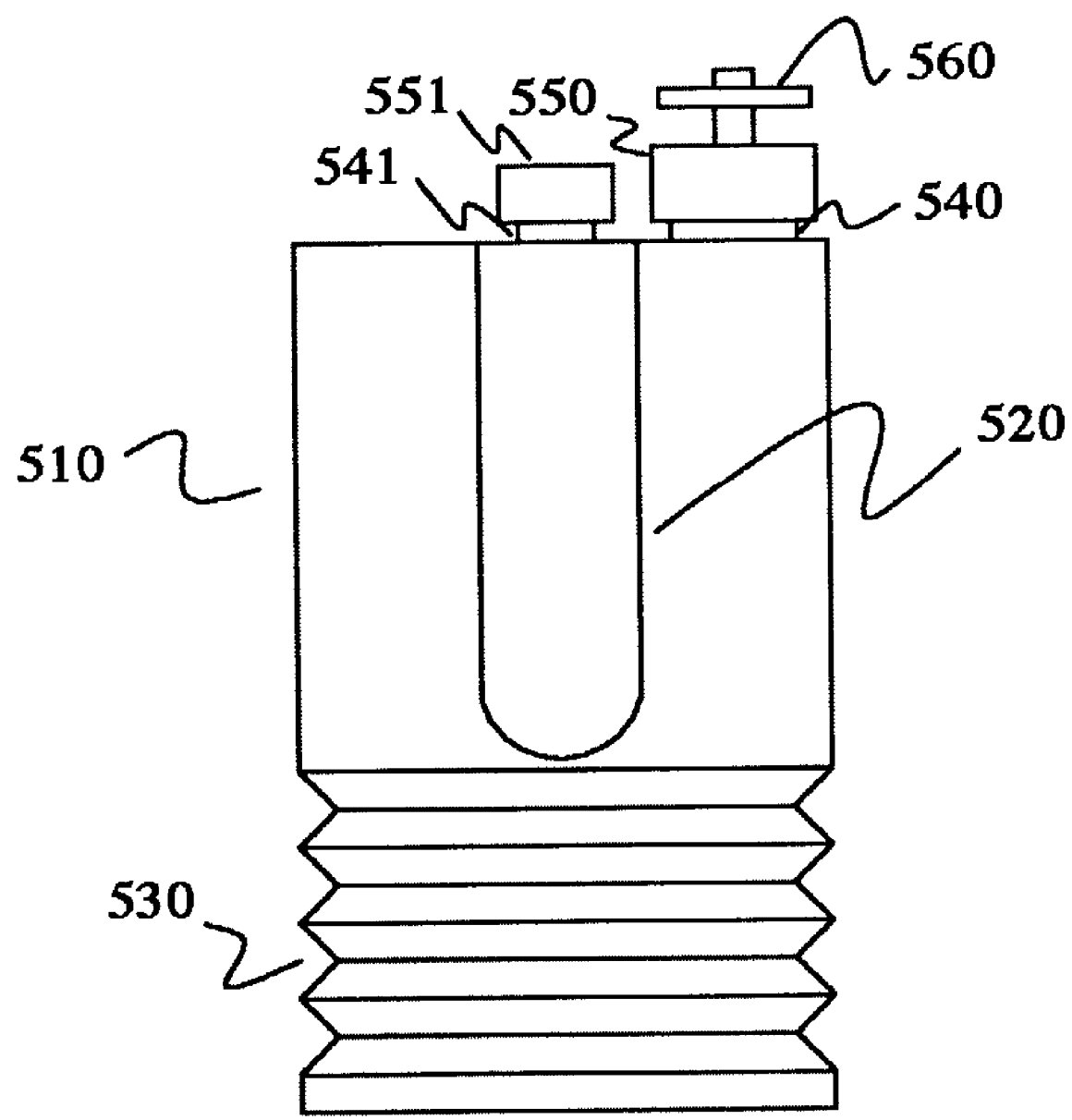
FIG. 5 shows a cell-cultivating device of a fifth embodiment of the present invention whereby the growth substrate means is a semi-permeable membrane bag and/or container and/or carrier.

Reference is made to FIG. 5, a cell-cultivating device of a fifth embodiment of the present invention which has a first chamber 510 containing a semi-permeable bag growth substrate means 520. Semi-permeable bag substrate 520 may be constructed from any material such as woven substrates, non-woven substrates, polyamide, polyester, polyurethane, fluorocarbon polymers, polyethylene, polypropylene, or polyvinyl alcohol. Semi-permeable bag substrate 520 allows the cells contained therein to be sufficiently oxygenated without being directly exposed to a gaseous environment through a thin air-growth medium interface. The semi-permeable bag or container substrate 520 may be optionally gas-permeable without allowing passage of cells.

The first chamber 510 of the present embodiment is connected to the second chamber 530, wherein first and/or second chamber may contain growth culture medium and both chambers are substantially open to each other at their interface. In the present embodiment, the second chamber 530 may be in the form of a compressible chamber such as a bellow, which may be compressed or released to move the growth culture medium from first chamber 510 to second chamber 530.

When the second chamber 530 is compressed, growth medium is substantially moved and/or forced into the first chamber 510, causing the cell-containing semi-permeable bag substrate 520 to be submerged in the growth media in order to allow cells to be nourished. When the second chamber 530 is not compressed, the growth medium substantially returned and/or remained in the second chamber 530 thus exposing semi-permeable bag substrate 520 to oxygenation in the first chamber 510. First chamber 510 may further comprise at least one opening 541 for loading cells into semi-permeable bag substrate 520 and fitted with a closing means 551 for reversibly sealing opening 541. First chamber 510 may also be additionally equipped with a second opening 540 for loading or withdrawing culture medium into or out of the first chamber 510 and for exchanging air with the external environment. The second opening 540 is reversibly sealed by a second closing means 550. Closing means 550 is optionally fitted with at least one air filter 560 to sterilize air passing in or out of the cell-cultivating device.

Figure 6A:
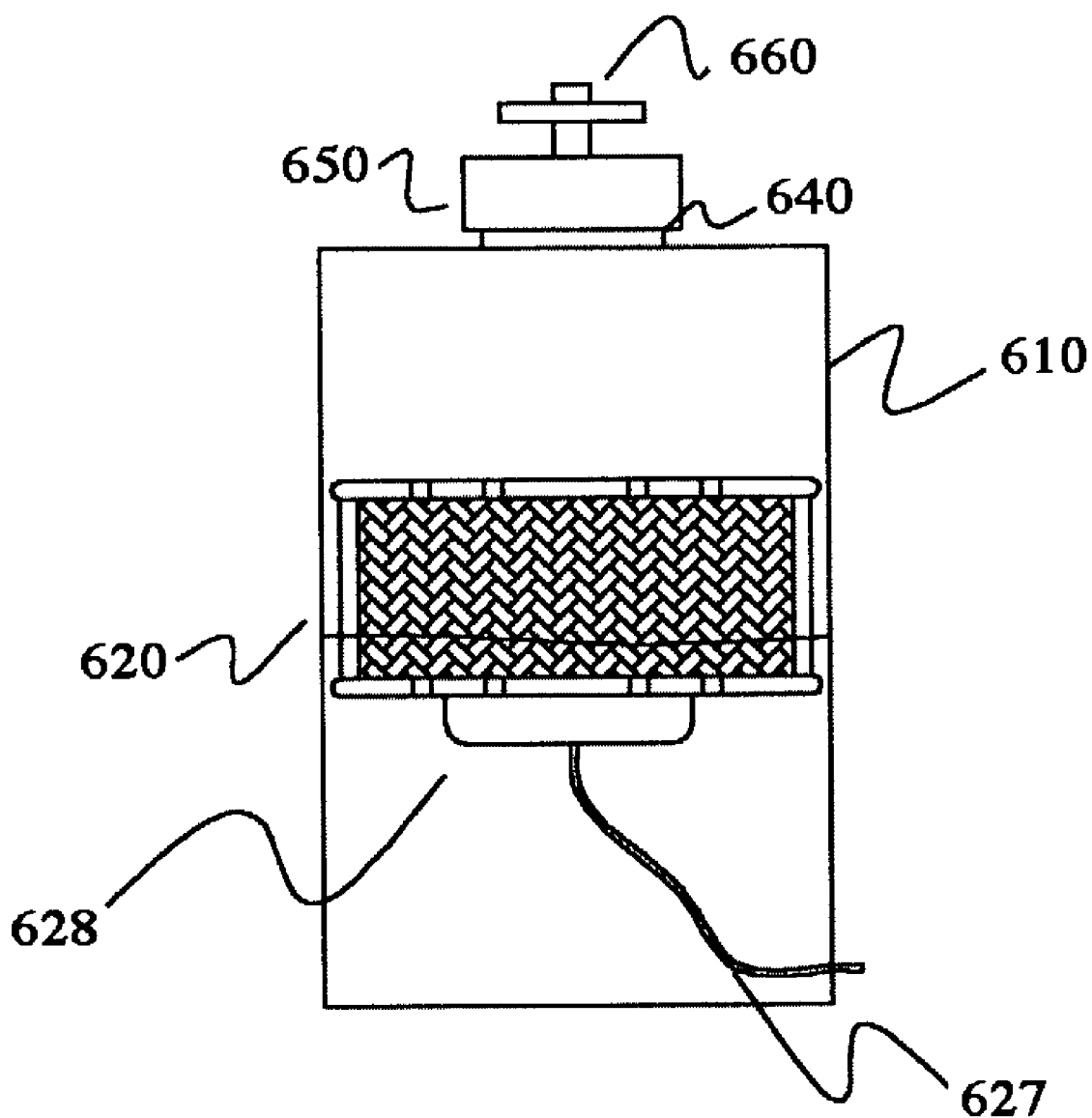
FIG. 6A shows a cell-cultivating device of a sixth embodiment of the present invention, wherein the growth substrate means in the first chamber floats above the growth medium and is indirectly exposed to a gaseous environment via a thin gas-liquid interface when an air-containing device such as a floating bag disposed in the second chamber is inflated.
Figure 6B:
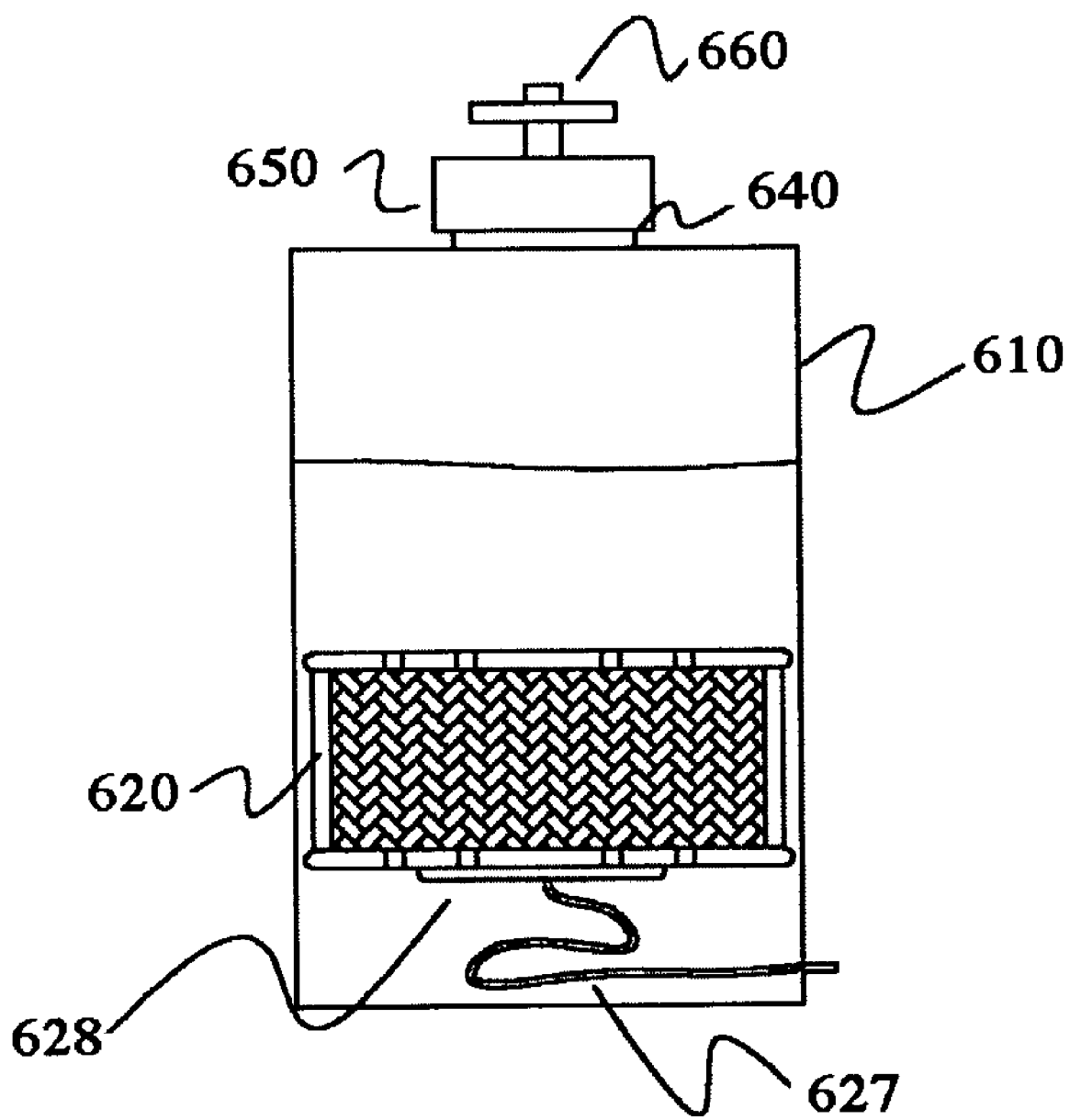
FIG. 6B shows a cell-cultivating device of the sixth embodiment of the present invention, wherein the growth substrate means is submerged in the growth medium when the air containing device such as a floating bag disposed within the second chamber is deflated.

Referring to FIGS. 6A and 6B, a cell-cultivating device of a sixth embodiment of the present invention. Culture chamber 610 having a growth substrate means 620 which floats on or submerge under the growth medium by controlling floating bag assembly 628 and an air tube 627. When floating bag assembly 628 is filled with air, as shown in FIG. 6A, growth substrate means 620 is substantially, but indirectly, exposed to a gaseous environment of culture chamber 610 and the cells contained within are exposed to oxygenation via a thin gas-growth medium interface. When floating bag 628 is substantially deflated, as shown in FIG. 6B, growth substrate means 620 is substantially submerged in the growth medium to allow cells adhered thereon to obtain nutrients.

Culture chamber 610 may optionally contain at least one opening 640 for loading or withdrawing growth medium into or out from culture chamber 610 and for exchanging air with the external environment. Opening 640 is reversibly sealed with a closing means 650. The closing means 650 further comprises at least one air filter 660 to sterilize air passing in or out of the cell-cultivating device.

Figure 7A:
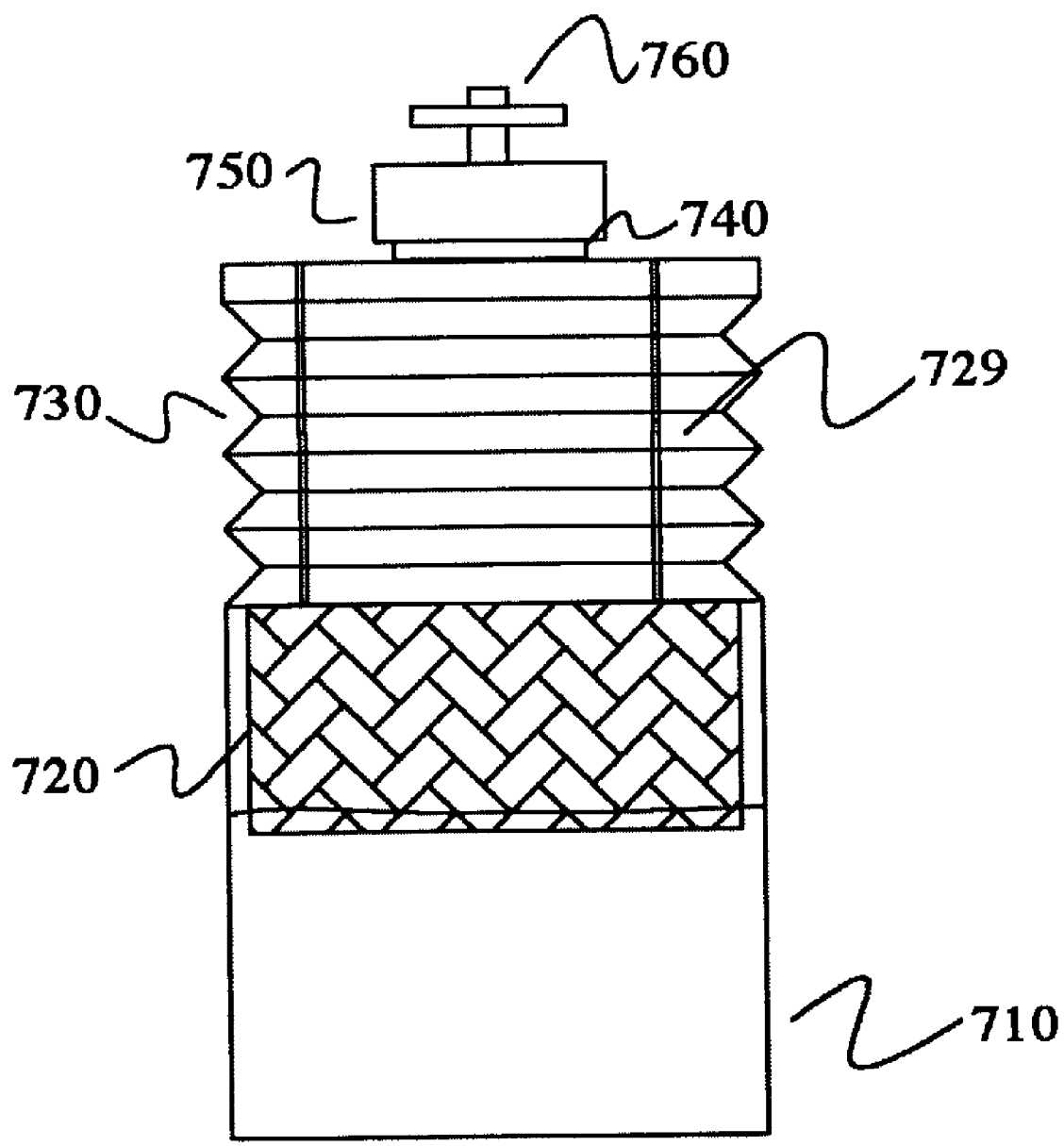
FIG. 7A shows a cell-cultivating device of a seventh embodiment of the present invention, wherein the movement of the growth medium in a lower chamber is controlled by a compressible upper chamber.
Figure 7B:
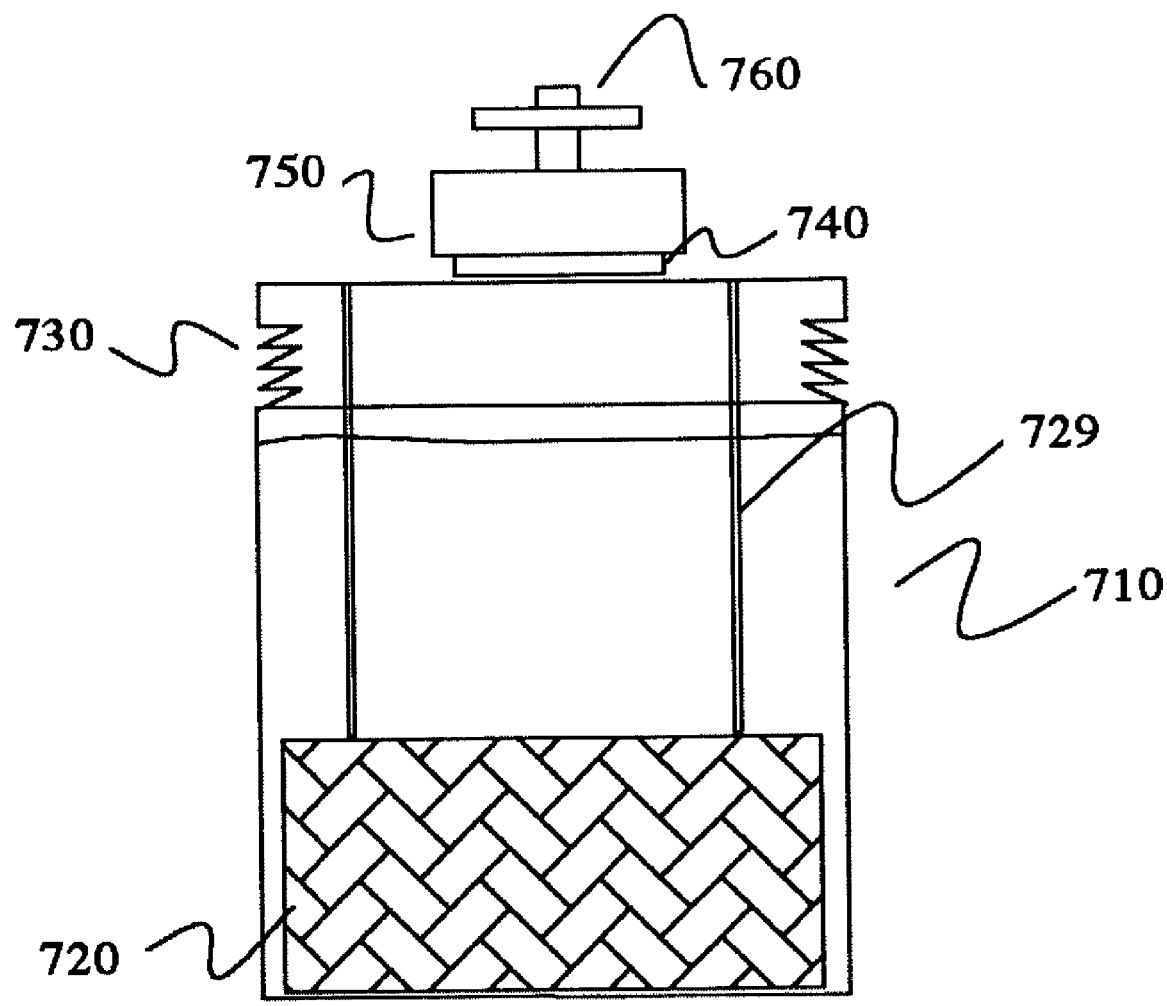
FIG. 7B shows a cell-cultivating device of the seventh embodiment of the present invention, wherein the substrate means in the lower chamber is submerged in the culture medium by compressing the upper compressible chamber.

Referring to FIGS. 7A and 7B, a cell-cultivating device of a seventh embodiment of the present invention. A first chamber 710 contains growth medium. A second chamber 730 is connected with and positioned atop first chamber 710. Second chamber 730 is connected to growth substrate means 720 through cable 729. Substrate means 720 may be constructed from any material such as ceramics, polymers, woven substrates, nonwoven substrates, polyamide, polyester, polyurethane, fluorocarbon polymers, polyethylene, polypropylene or polyvinyl alcohol, glass, silica and DEAE. In the seventh embodiment, the growth substrate means 720 may optionally be porous. The porous growth substrate means allows the cells contained thereon to be oxygenated without being directly exposed to the shear force of an air stream or air bubbles in the gaseous environment. Direct exposure of cells, particularly animal cells and/or mammalian cells can be harmful and can lead to cell death and loss of viability of the culture.

The growth substrate means 720 can be of any form, shape or size including but not limited to a disk, flake, block, plate, sheet, strip, pellet, microcarrier, semi-permeable pellet, macroscopic pellet, semi-permeable membrane, or semi-permeable hollow fiber.

First chamber 710 is connected to the second chamber 730, wherein first and/or second chamber may contain growth medium and both chambers can communicate directly at their interface. In this seventh embodiment, second chamber 730 may be in the form of a compressible chamber such as a bellow and can be compressed or decompressed. FIG. 7A shows second chamber 730 in a decompressed form. FIG. 7B depicts second chamber 730 in a compressed form. When the second chamber 730 is compressed, the growth substrate means 720 is lowered and submerged into the growth medium contained in the first chamber 710 such that growth substrate means 720 is substantially submerged in the growth medium, as depicted in FIG. 7B. When second chamber 730 is not compressed, the substrate means 720 emerges from growth culture medium contained in first chamber 710 such that growth substrate means 720 is substantially, but indirectly, exposed to the gaseous environment of second chamber 730 via a thin gas-growth medium interface to receive oxygen. Second chamber 730 further comprises at least one opening 740. Opening 740 is reversibly sealed with a closing means 750. Closing means 750 further comprises at least one air filter 760 to sterilize air passing in or out of the cell-cultivating device.

Figure 8:
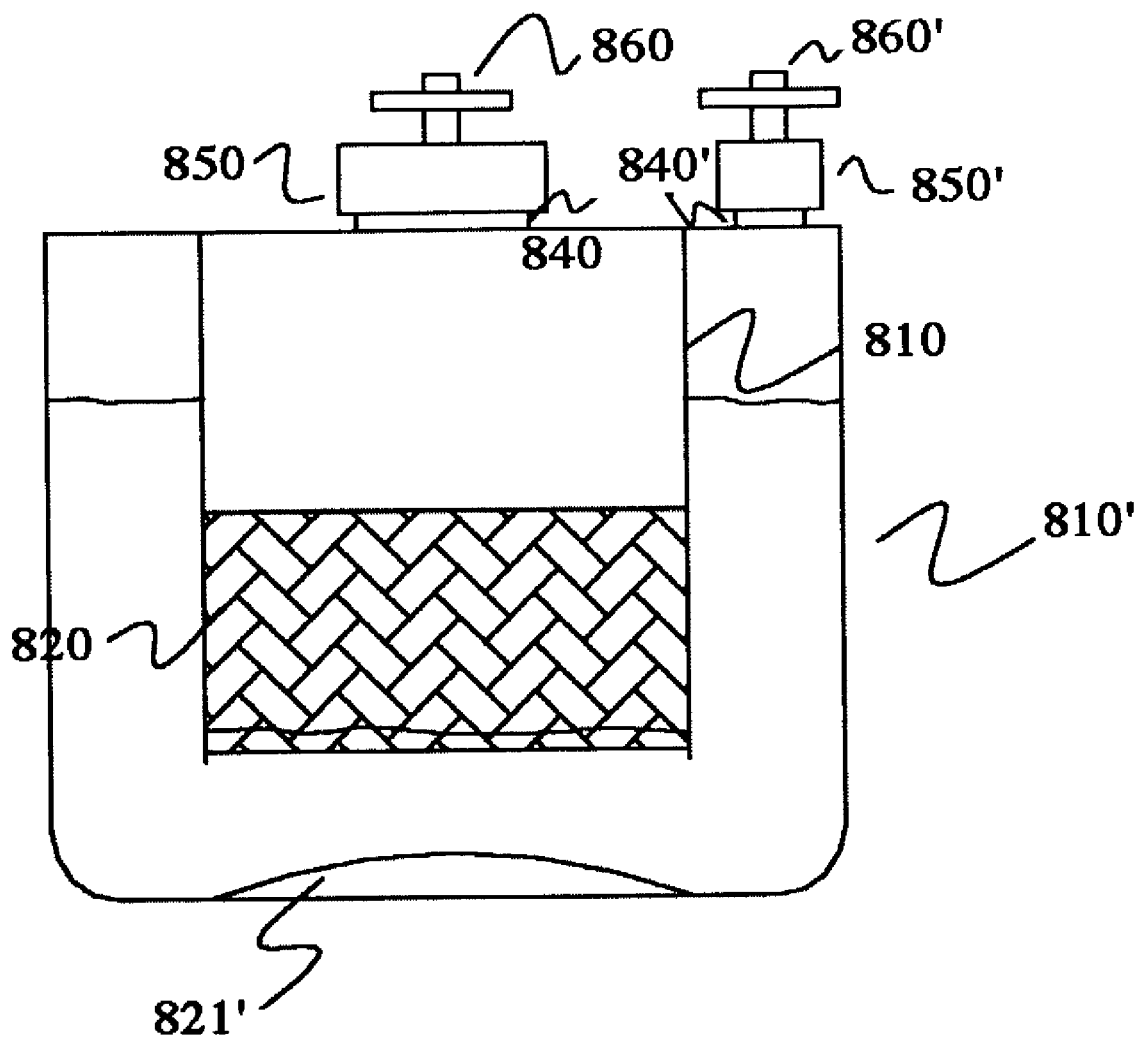
FIG. 8 shows a cell-cultivating device of an eighth embodiment of the present invention, wherein the medium level in a first chamber is controlled by air pressure in a second chamber and that the second chamber is in surrounding relationship with the first chamber.

Reference is made to FIG. 8, which shows a cell-cultivating device of an eighth embodiment of the present invention. The device shows two culture chambers 810 and 810', wherein chamber 810 is place inside chamber 810' and chamber 810' is in surrounding relationship with chamber 810. Chamber 810 contains a substrate means to receive cells and is substantially open at its bottom end such that growth culture medium from chamber 810' is free to move from chamber 810 to chamber 810' and vice versa through the bottom of chamber 810. The bottom surface of chamber 810' has a contour 821' optimally designed such that the flow is streamlined and it eliminates the accumulation of cells that failed to adhere to the growth substrate means 820.

Chamber 810 may further comprise at least one opening 840 for loading or withdrawing cells and/or culture medium into or out of culture chamber 810. The opening 840 is reversibly sealed by a closing means 850. Closing means 850 further comprises at least one air filter 860 to sterilize air passing in or out of the cell-cultivating device. Chamber 810' further comprises at least one opening 840', which is fitted by a second closing means 850'. Closing means 850' further comprises at least one air filter 860 to sterilize air passing in or out of the cell-cultivating device.

Growth medium level in chamber 810 is controlled by pumping air through air filter 860' into chamber 810' to vary the air space in chamber 810'. This pressure drives the growth medium from chamber 810' into chamber 810. Growth substrate means 820 is substantially submerged in growth medium when air chamber 810' is decreased. When the air in chamber 810' is increased, the vacuum in chamber 810' causes the growth medium to substantially return to chamber 810' thus causing growth substrate means 820 to be indirectly exposed to the gaseous environment of chamber 810 via a thin gas-growth medium interface.

Figure 9A:
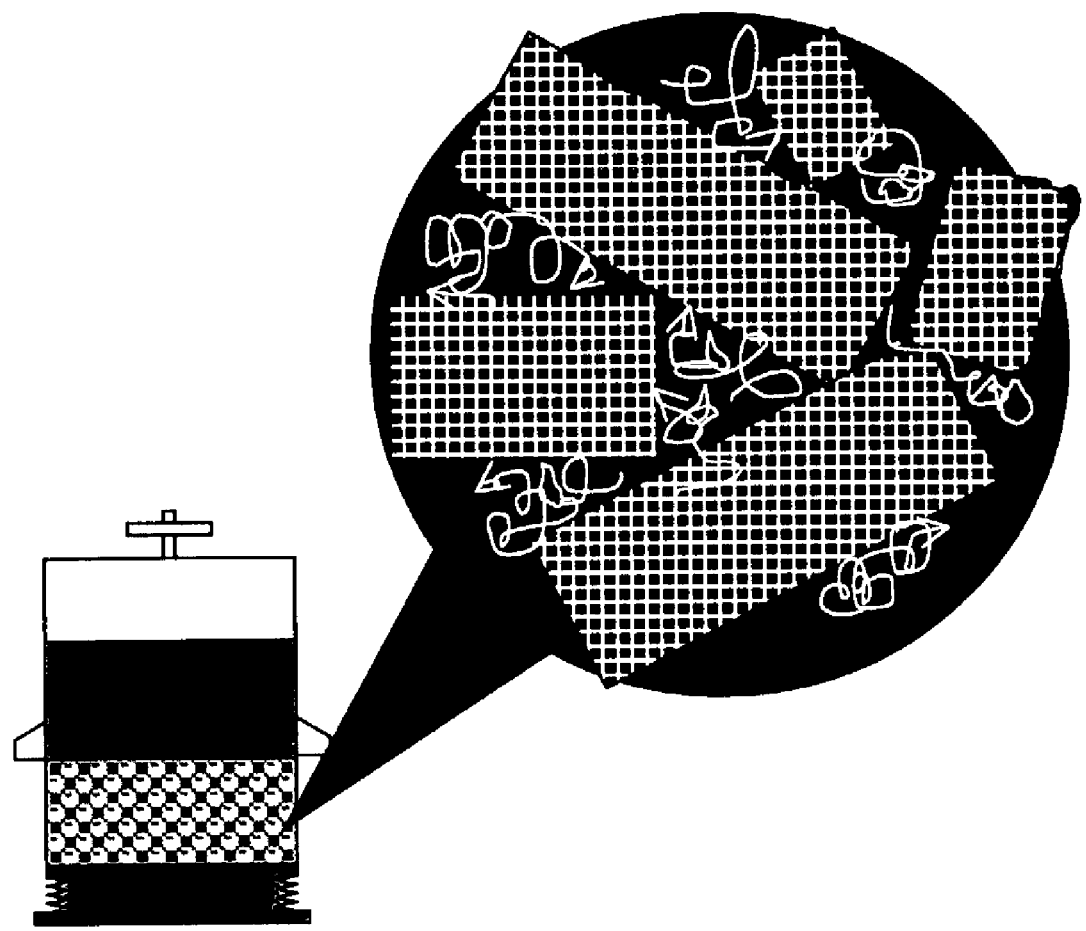
FIG. 9A shows a growth substrate means of the present invention when the growth substrate is submerged in the growth medium by compressing the compressible second chamber.

FIG. 9A shows the growth substrate means 120 of the present invention when the growth substrate means is submerged in the growth medium and the nutrient availability is high. The submersion of the optionally porous growth substrate creates a phenomenon termed static mixing which is a gentle mixing of growth medium and thus, nutrients within the growth substrate means 120 to help redistribute cells that have become dislodged and to also redistribute cells evenly.

Figure 9B:
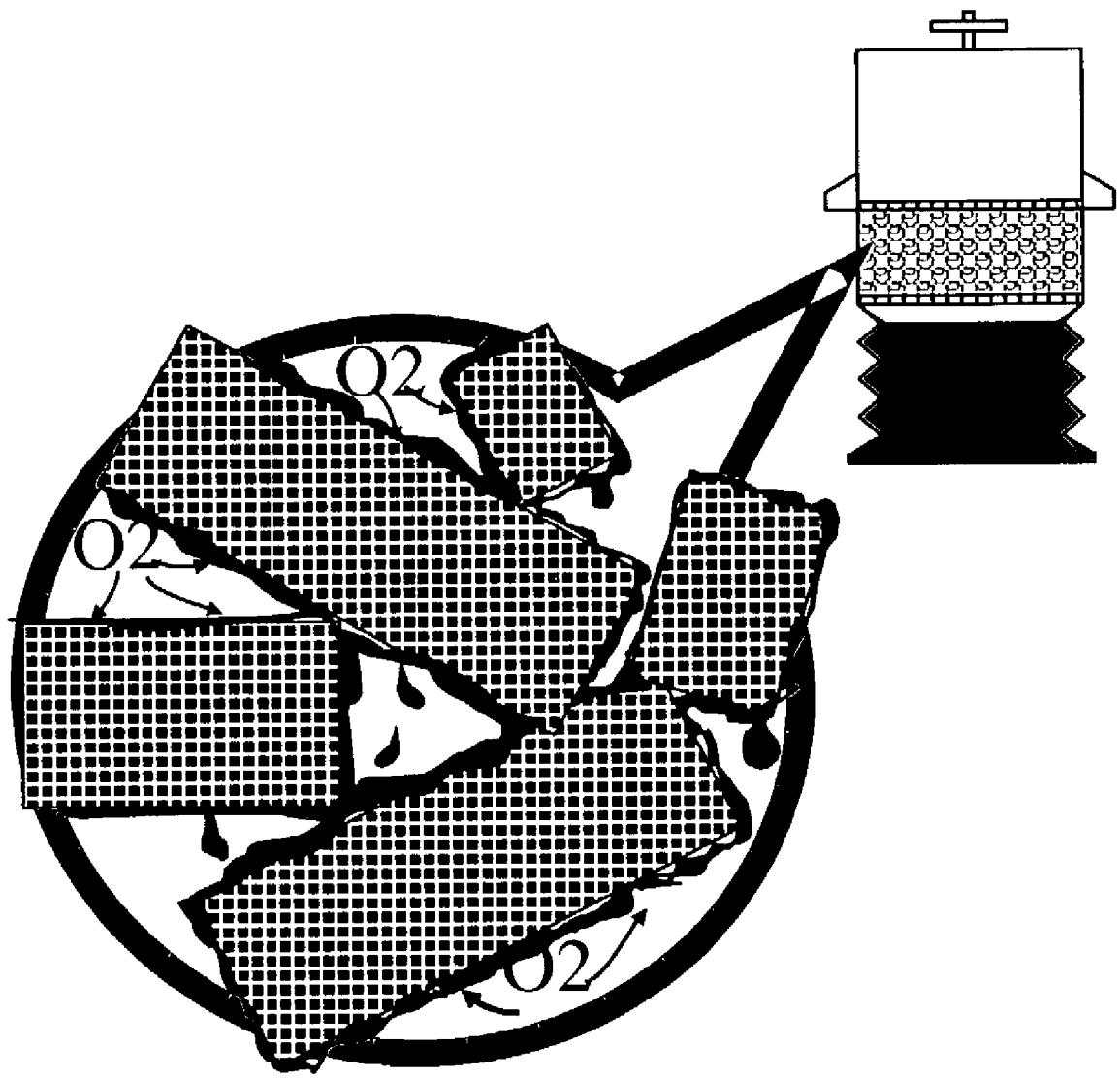
FIG. 9B shows the growth substrate means of the present invention when the growth substrate means is indirectly exposed to a gaseous environment through a thin gas-growth medium interface and oxygen availability is high by decompressing the compressible second chamber.

FIG. 9B shows the substrate means 120 of the present invention when the growth medium level is lower than the substrate means 120 and oxygen availability is high. The figure depicts that upon removal of the growth medium from the chamber containing the growth substrate 120, a thin layer of growth medium remains on the surface of the porous growth substrate. This thin layer protects the cells contained on and/or in the growth substrate 120 to be oxygenated without being directly exposed to the shear force of air stream in gaseous environment.

Figure 10A:
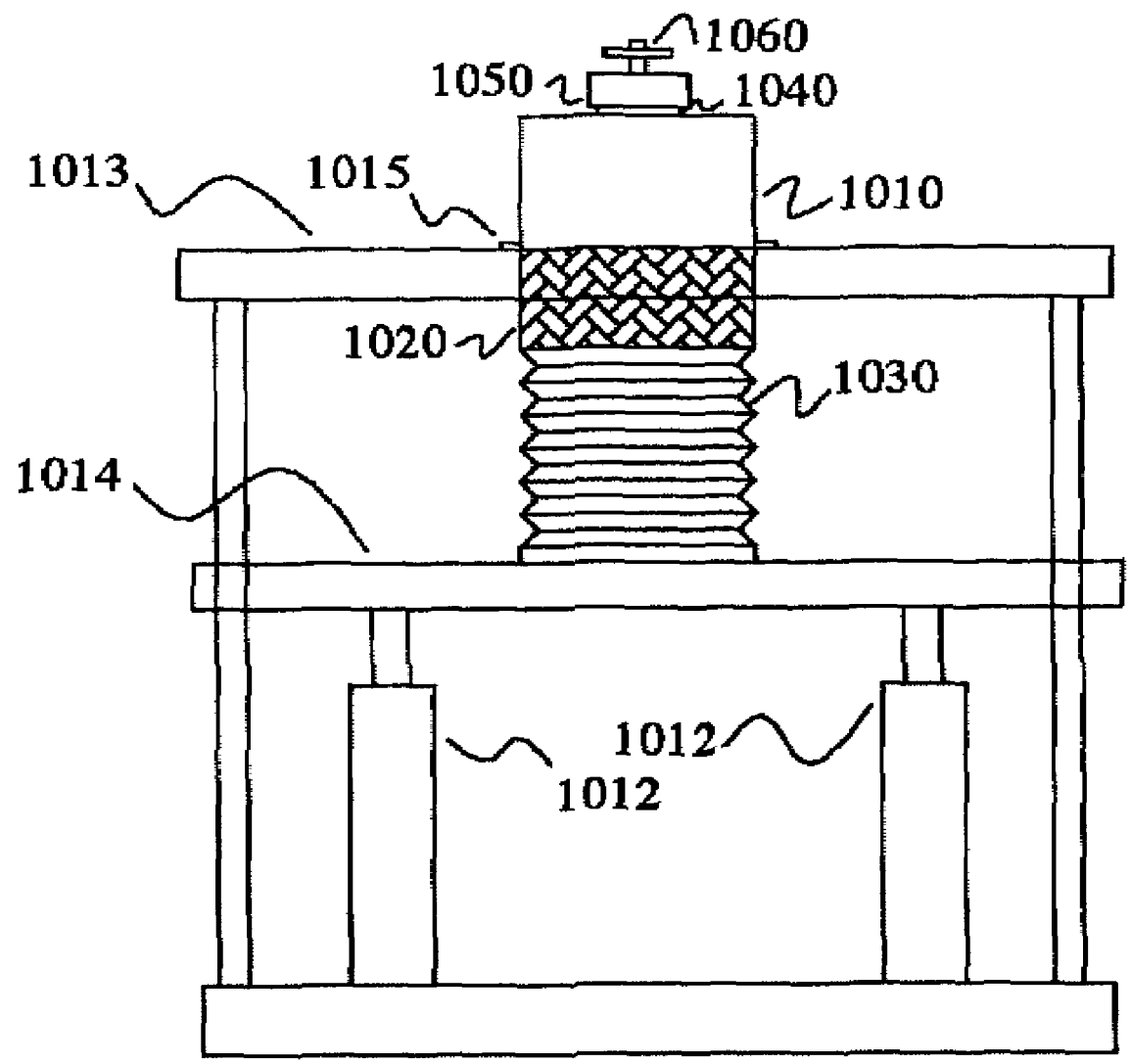
FIG. 10A shows a cell-cultivating device of a ninth embodiment incorporating the configuration of the first embodiment of the present invention wherein the movement of the second chamber is controlled by a piston mechanism and when the second chamber is not compressed, the growth medium remained in the second chamber.
Figure 10B:
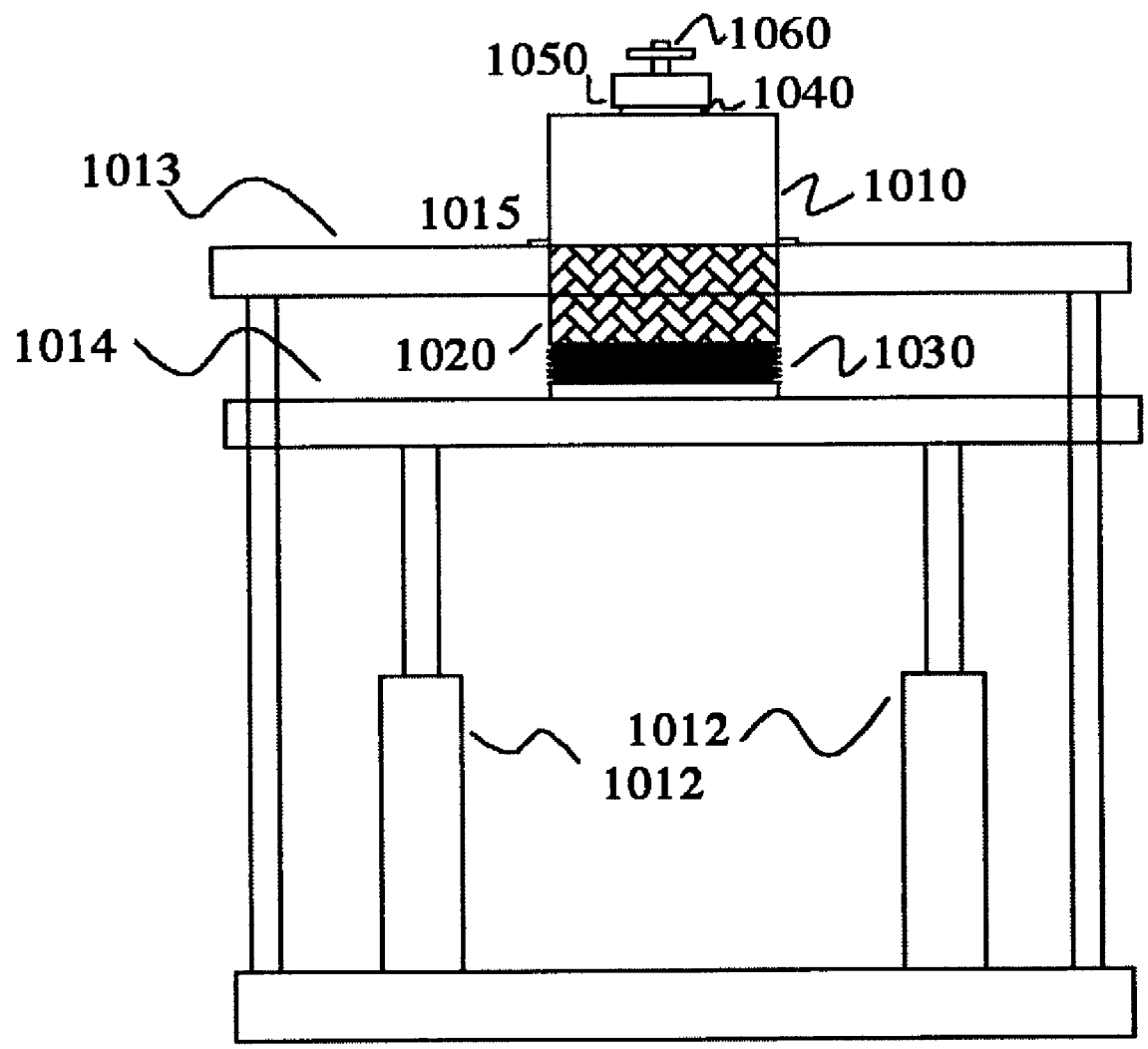
FIG. 10B shows a cell-cultivating device of the ninth embodiment incorporating the configuration of the first embodiment in accordance with the present invention whereby the second chamber is compressed by the piston mechanism.

FIGS. 10A and 10B depict a nineth embodiment of the instant invention. The embodiment of FIGS. 1A and 1B is depicted in cooperation with a driving device such as an oil pressure cylinder or an air pressure cylinder, depicted as 1012 mounted on the bottom of second chamber 1030, which is compressible. When the pressure cylinder 1012 rises, as depicted in FIG. 10B, or drops, as depicted in FIG. 10A, second chamber 1030 is intermittently and periodically compressed and decompressed. Compression and decompression of the second chamber 1030 causes growth substrate means 1020 to move intermittently and periodically from chamber 1030 into chamber 1010 and vice versa. Thus either submerged the growth substrate 1020 in the culture medium to receive nutrients or emerged from the growth medium to allow cells on the growth substrate 1020 to receive oxygen.

Figure 11A:
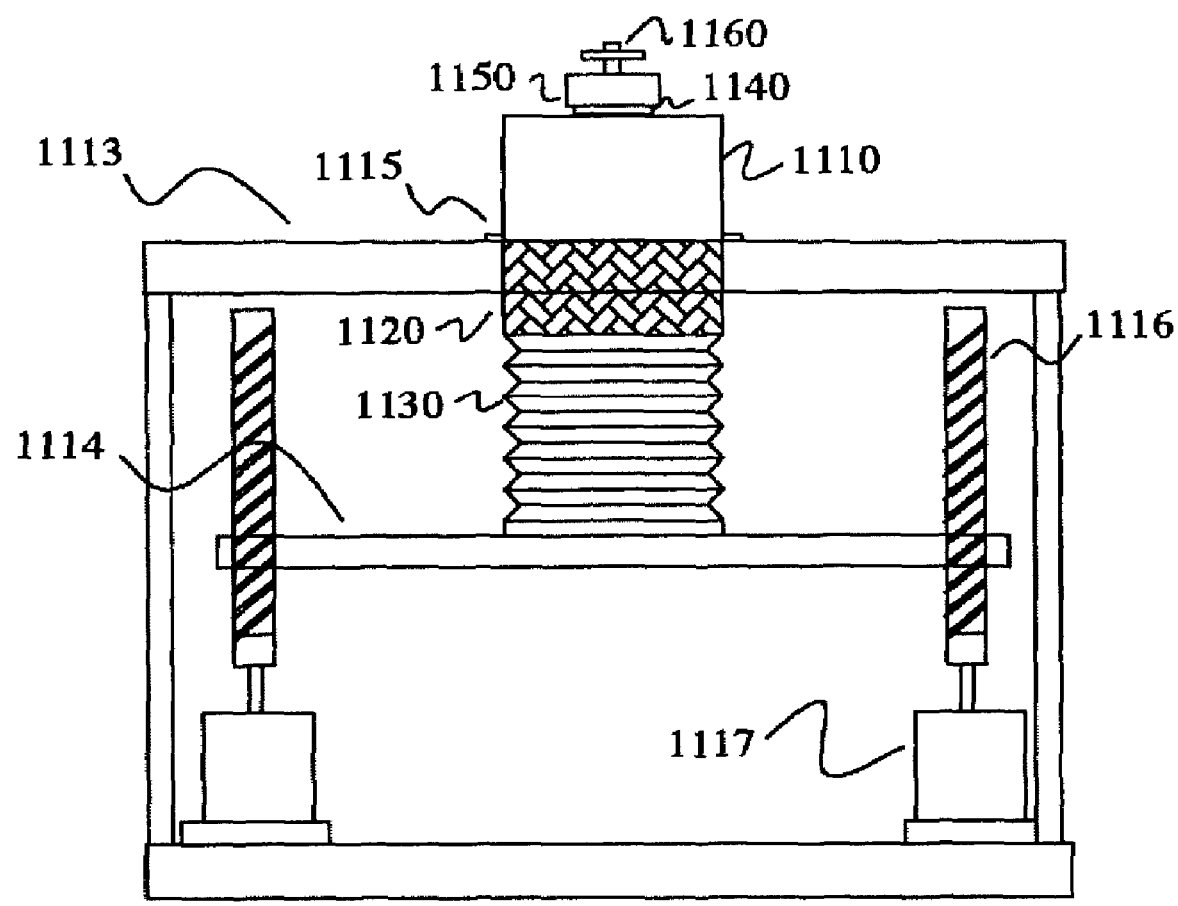
FIG. 11A shows a cell-cultivating device of a tenth embodiment incorporating the first embodiment of the present invention, whereby the screw jack assembly is used as a driving means to decompress the second chamber.
Figure 11B:
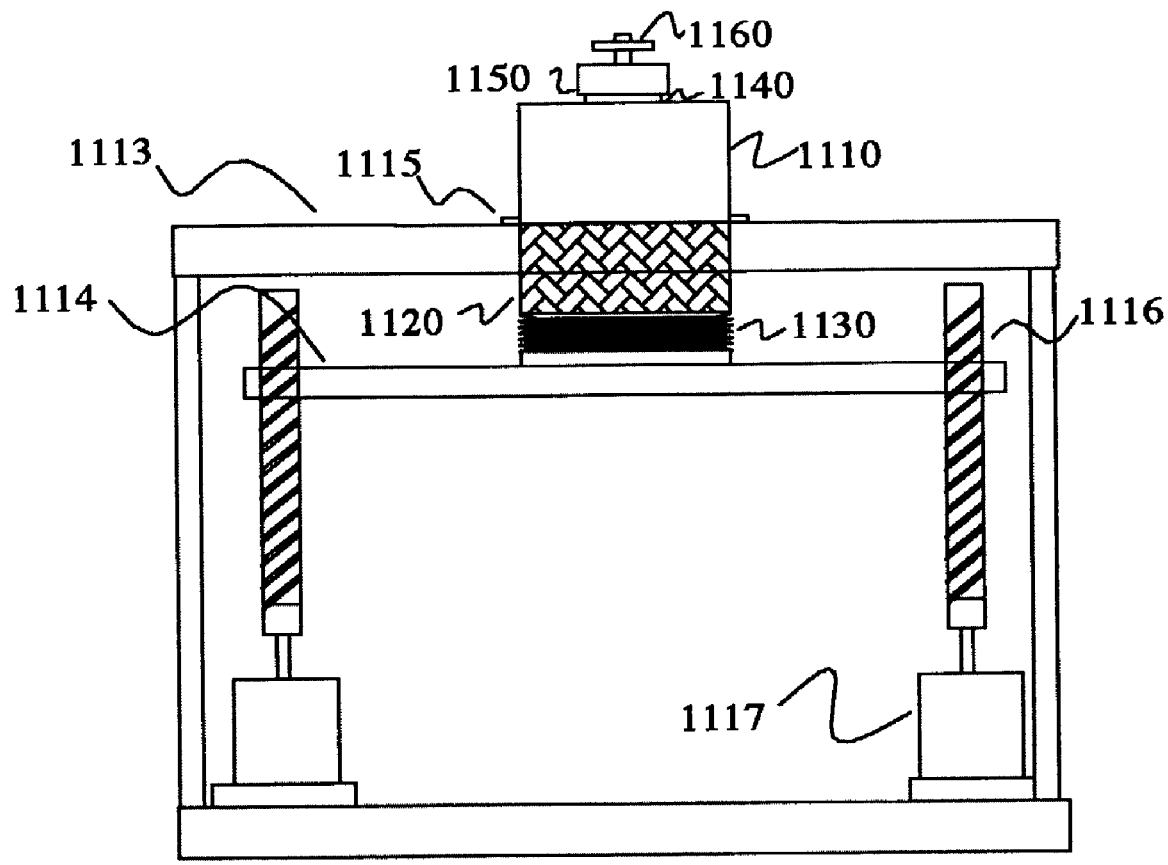
FIG. 11B shows a cell-cultivating device of the tenth embodiment incorporating the first embodiment of the present invention, whereby the screw jack assembly is used to compress the second chamber in order to move the culture medium from the second chamber into the first chamber.

FIGS. 11A and 11B depict a tenth embodiment of the instant invention. The embodiment of FIGS. 1A and 1B are depicted in cooperation with a volume-adjusting mechanism such as a screw jack, depicted as 1117 mounted on the bottom of the second chamber 1130, which has a compressible component. When the screw jack 1117 rises, as depicted in FIG. 11B, or drops as depicted in FIG. 11A, the second chamber 1130 is periodically and alternately compressed and decompressed. Compression and decompression of the second chamber 1130 cause growth substrate means 1120 to be periodically and intermittently submerged in growth medium and then indirectly exposed to the gaseous environment via a thin gas-growth medium interface for oxygenation.

Figure 12A:
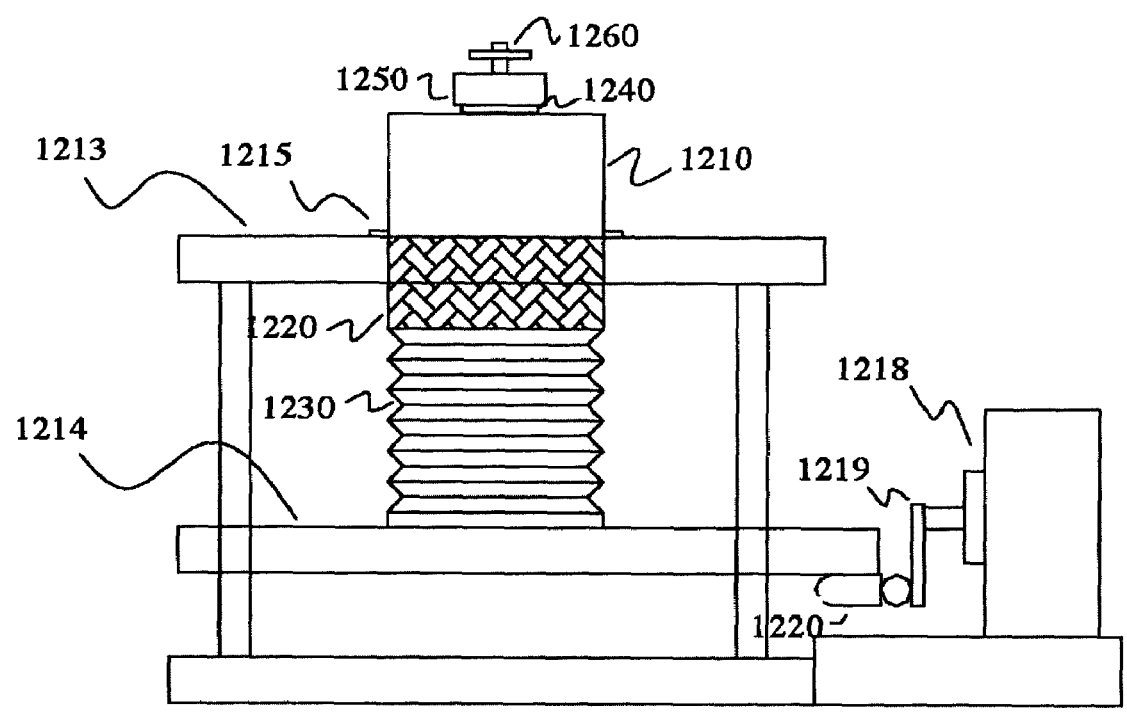
FIG. 12A shows an eleventh embodiment of the present invention, whereby a driving means is used to decompress the growth medium containing chamber.
Figure 12B:
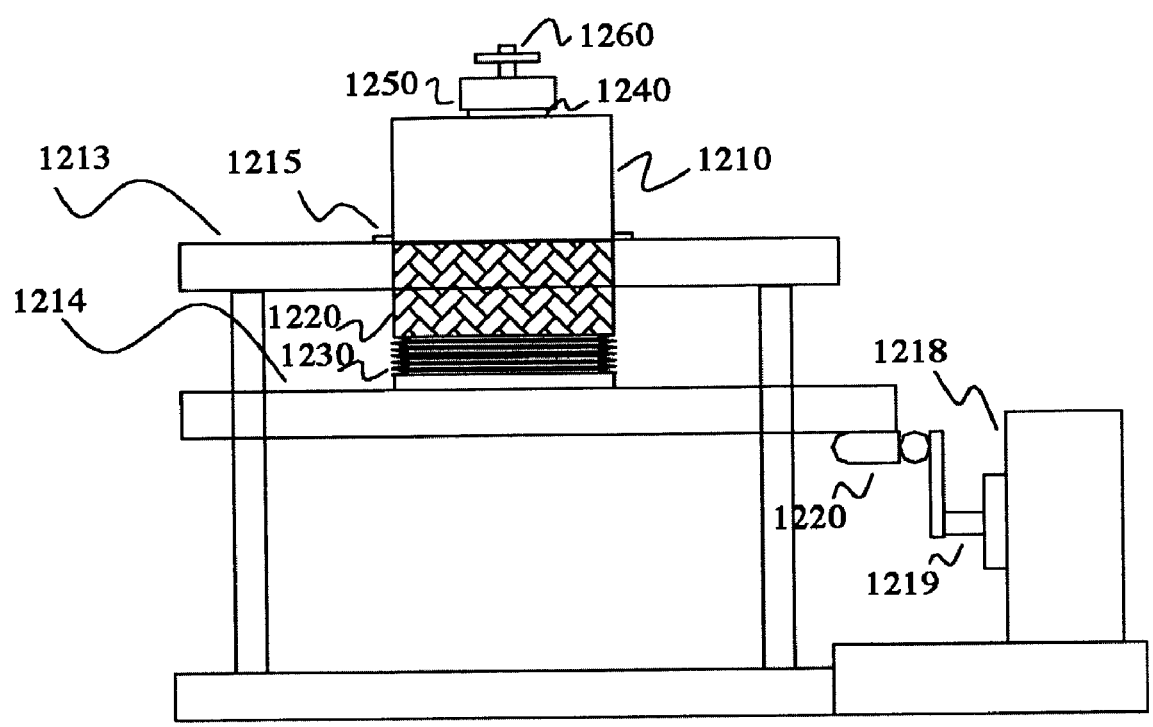
FIG. 12B shows the eleventh embodiment of the present invention, whereby the driving means is used to compress the growth medium containing second chamber in order to move growth medium from the second chamber into the first chamber.

FIGS. 12A and 12B depict an eleventh embodiment of the instant invention. The embodiment of FIGS. 1A and 1B are depicted in cooperation with a driving device such as a motor or a step motor 1218 connected to a volume-adjusting mechanism such as a shaft driver 1219 and 1220 mounted on the bottom of the second chamber 1230 which is compressible. When the shaft driver rises, as depicted in FIG. 12B, or drops, as depicted in FIG. 12A, second chamber 1230 is periodically and intermittently compressed and decompressed. Compression and decompression of the second chamber 1230 causes growth substrate means 1220 of the first chamber 1210 to be periodically and intermittently submerged in or emerged from the growth medium.

Figure 13A:
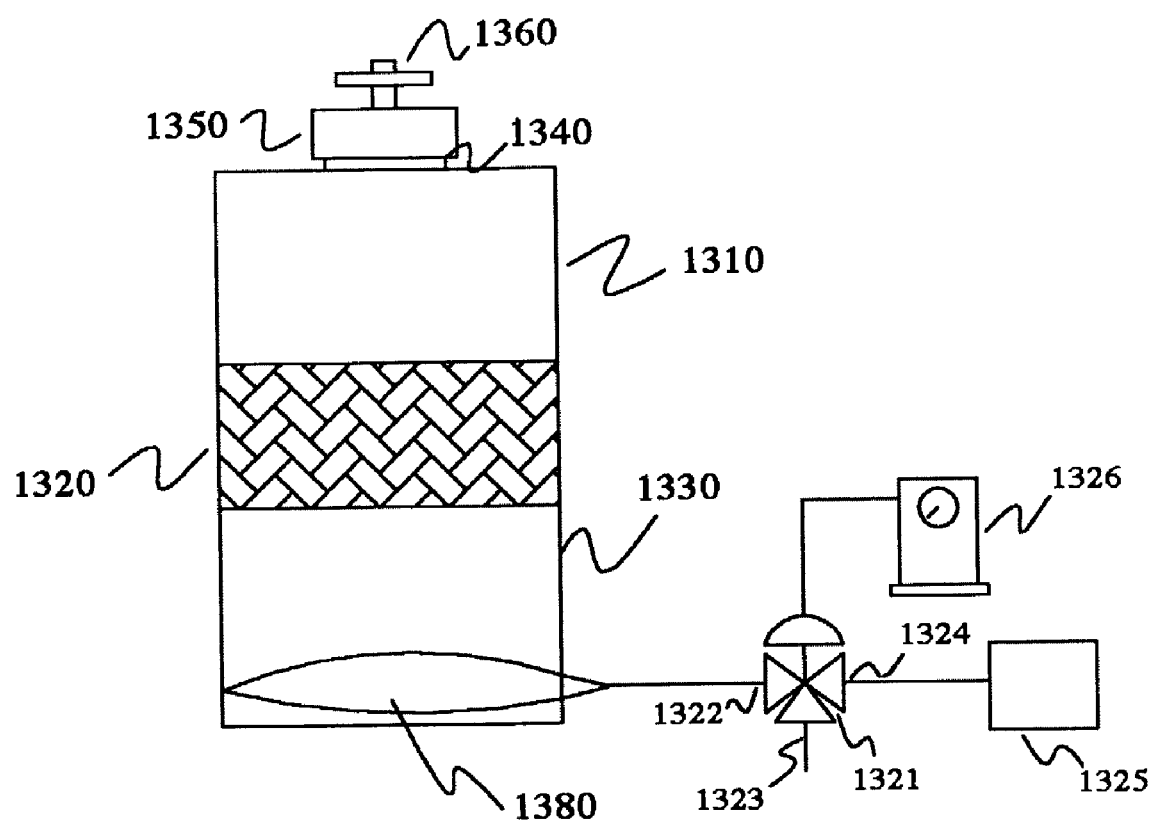
FIG. 13A shows a twelfth embodiment of the present invention, whereby a driving means is a balloon as described in FIGS. 2A and 2B of the present invention.
Figure 13B:
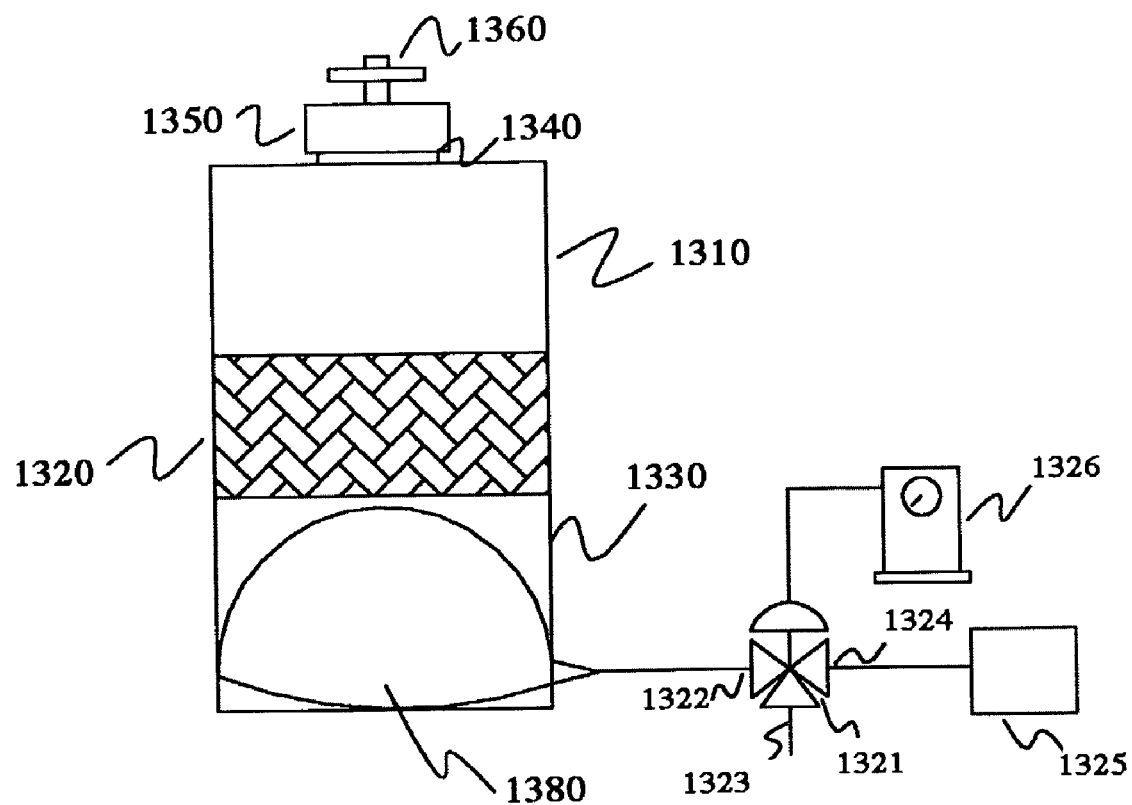
FIG. 13B shows the twelfth embodiment of the present invention whereby the driving means for culture medium is the balloon as described in FIGS. 2A and 2B to the second embodiment of the present invention. These figures show the balloon in an inflated state.

FIGS. 13A and 13B depict a twelveth embodiment of the instant invention. The embodiment of FIG. 2 is shown in cooperation with an air compressor driving device. The valve port 1322 can be maintained in an open state. When valve port 1324 is opened and valve port 1323 is closed, air is driven by air pump 1325 into balloon 1380 causing it to be filled with air. Consequently, as shown in FIG. 13B, the volume for the culture medium in the second chamber 1330 is reduced. Thus, growth medium is expelled from second chamber 1330 into first chamber 1310 causing growth substrate 1320 to be substantially submerged in the growth medium. The switch of solenoid valve ports 1323 and 1324 can be controlled by, for example, a timer controller 1326. The timer controller 1326 changes the open/closed status of the solenoid valves 1323 and 1324. When valve port 1324 is closed, and valve port 1323 is opened, air in the balloon is forced out by the pressure of culture medium due to gravity. Growth medium thus flows down from the first chamber 1310 to the second chamber 1330 causing growth substrate 1320 to be exposed to the air. Alternating the inflation and deflation of balloon 1380 results in periodic and intermittent submersion of growth substrate 1320 in growth medium and emergence of the growth substrate 1320 from the culture medium and indirect exposing the growth substrate means 1320 to the gaseous environment via a thin gas-growth medium interface.

Figure 14:
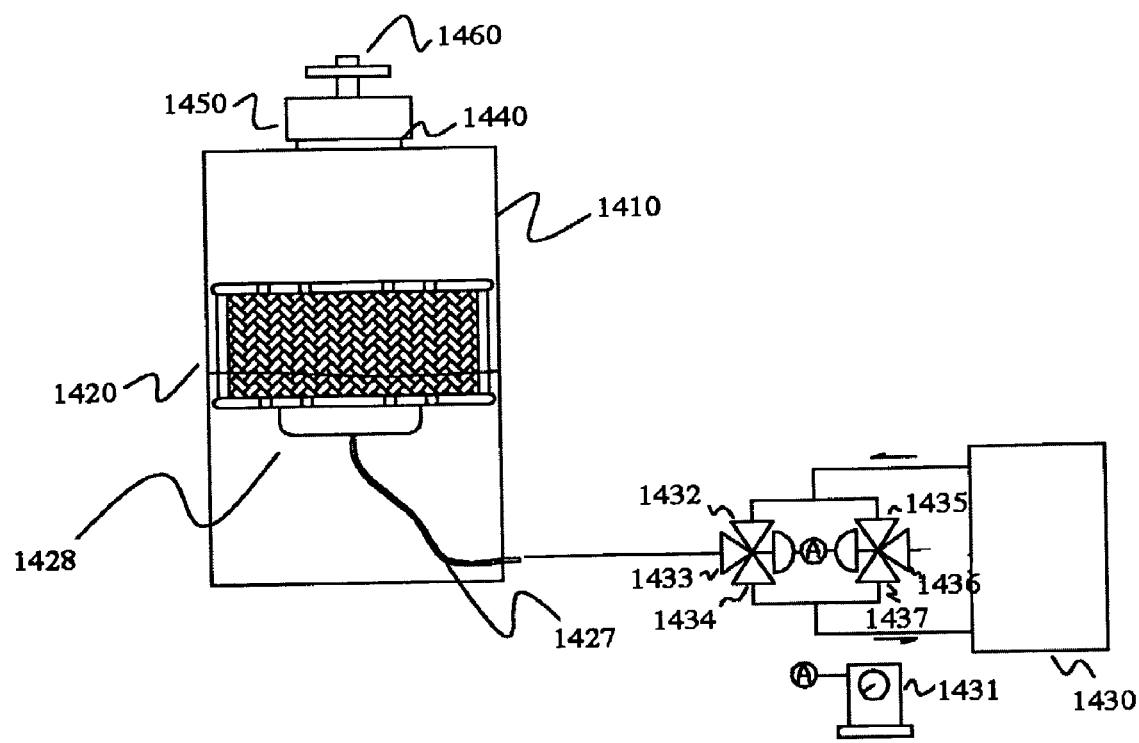
FIG. 14 shows a thirteenth embodiment of the present invention whereby a different driving means for the cell-cultivating device is employed to drive the volume-adjusting means to move the growth medium from one chamber to another.

FIG. 14 depicts a thirteenth embodiment of the instant invention. The embodiment depicted in FIG. 6 is shown in cooperation with an air compressor driving means. The substrate means 1420 can float above or be submerged in growth medium by controlling the amount of air in the floating bag 2148 and air tube 1427. Balloon 1428 is attached to bottom of growth substrate means 1420 and is filled with air or emptied by driving devices such as air pump 30 connected to at least one solenoid valve port. In operation, the valve ports 1433 and 1436 are always open. When valve ports 1432 and 1437 are opened, and valve ports 1434 and 1435 are closed, air is driven by air pump 1430 into balloon 1428 and fills the balloon 1428. Growth substrate means 1420 therefore propels upward and indirectly exposing cells to the gaseous environment of first chamber 1410 via a thin gas-growth medium interface. The switching of solenoid valves can be controlled by, for example, a timer 1431. The timer 1431 changes the open/closed status of the solenoid valve ports. When valve ports 1432 and 1437 are closed, and valve ports 1434 and 1435 are opened, air in balloon 1428 is vacuum out by air pump 1430. Substrate means 1420 will then become substantially submerged in the medium.

Figure 15:
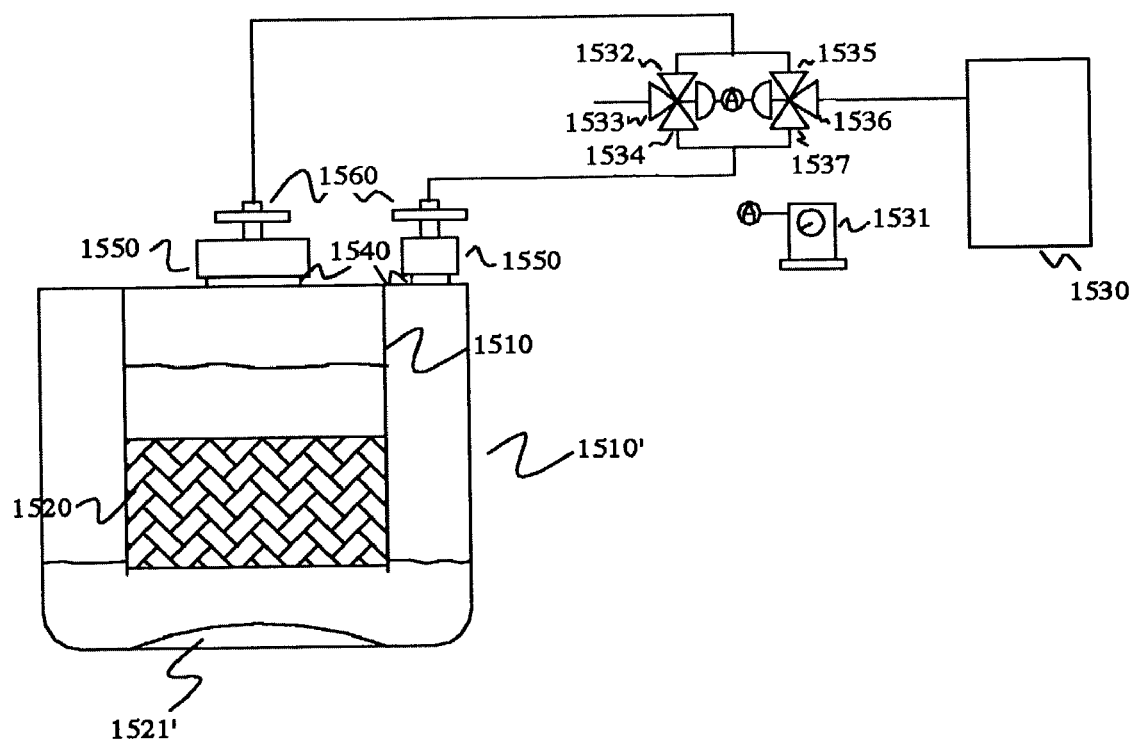
FIG. 15 shows a fourteenth embodiment of the present invention employing yet another driving means for the cell-cultivating device incorporating the configuration of the sixth embodiment of the present invention whereby when the pressure in the outer chamber is higher than in the inner chamber, the growth medium is moved substantially from the outer chamber into the inner chamber.

FIG. 15 depicts a fourteenth embodiment of the present invention. The embodiment depicted in FIG. 8 is shown in cooperation with an air compressor driving device. Valve ports 1533 and 1536 open. When valve ports 1534 and 1535 of the solenoid valve ports are open, the other valve ports, 1532 and 1537, are closed. Air is pushed into an inner surface of the first chamber 1510 by an air compressor 1530. Thus, the growth medium level in the first chamber 1510 decreases due to air pressure. Because the lower ends of the two chambers 1510 and 1510' are in communication with each other, the medium level in the culture chamber 1510' goes up when the medium level in the culture chamber 1510 goes down and vice-versa. The switch of solenoid valve can be controlled by a timer 1531. The timer 1531 can operate to open and close the solenoid valves. Next, the valve ports 1532 and 1537 are opened and the valve ports 1534 and 1535 are closed, and the valve ports 1533 and 1536 are still open without change. Then, air is pushed into the outer culture chamber 1510' so that the growth medium level in the culture chamber 1510' decreases. Meanwhile, the medium level in the culture chamber 1510 increases. By repeating this operation the culture medium in the chambers 1510 and 1510' periodically and intermittently moves from one chamber to another causing growth medium substrate 1520 to be submerged in the growth medium allowing cells to obtain nutrients or emerged from the growth medium allowing the cells to receive oxygenation via a thin gas-growth medium interface.

Figure 16:
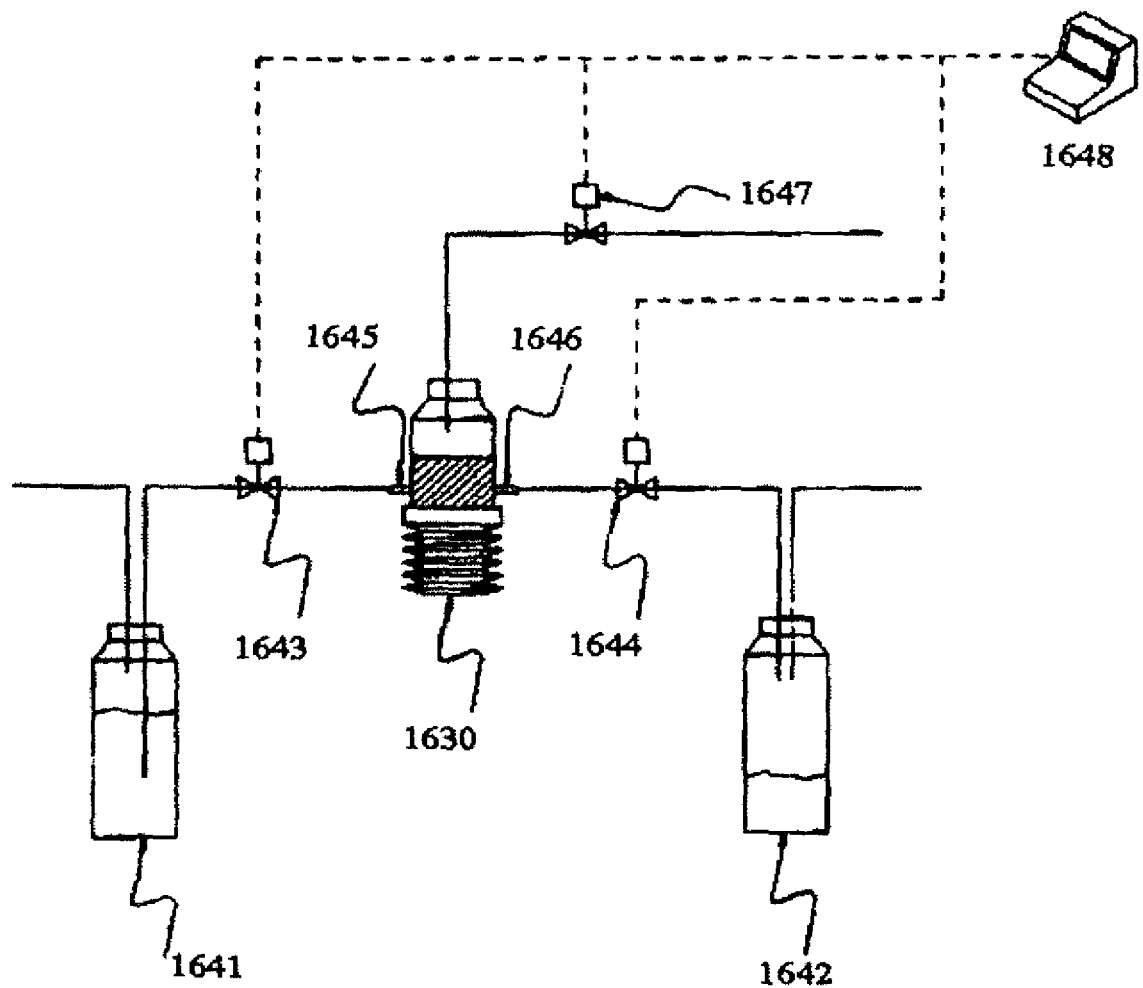
FIG. 16 shows a fifteenth embodiment of the present invention incorporating the cell-cultivating device of the first embodiment and further contains two reservoirs connected to the cell cultivating device in accordance with the present invention in order to replenish fresh culture medium for cultured cells and to collect cellular products dissolved in the spent culture medium contained in the cell cultivating device via connectors and/or tubings.

FIG. 16 depicts a fifteenth embodiment of the present invention. The embodiment depicted in FIG. 1 is shown in cooperation with a medium-exchange system. The medium-exchange system is meant to work in two different modes: medium-exchange mode and growth mode. In growth mode, valves 1643 and 1644 are closed, thereby closing connectors 1645 and 1646. Also, valve and air inlet 1647 are open to allow air exchange with the embodiment of FIG. 1 through air filter 160 (not shown). In this state, the growth medium cannot enter nor exit the cell-cultivating device. Once the medium is spent and/or sufficient secreted protein is produced by the cell culture, it is desirable to collect the spent medium for harvesting the protein and also to replenish the spent medium with fresh medium.

In medium exchange mode, valve and air inlet 1647 are closed. Further, valve 1643 is closed. Using the remaining gas pressure of the first chamber 110 in cooperation with compressing the second chamber 130 (e.g. bellow), valve 1644 is opened, which allows for the release of the spent medium out through connector 1646 and into storage container 1642. Following release of the spent medium, valve 1644 is closed. Next, by opening valve 1643, a suction is formed to draw the fresh medium contained in a storage container 1641 into second chamber 1630 through connector 1645. This expansion of second chamber 130 draws in fresh medium from storage flask 1641 through connector 1645 into the cell-cultivating device. Once a sufficient amount of fresh medium has been delivered, valve 1643 is closed. To reestablish normal growth mode, valve and air inlet 1647 are opened. All valve controls can be powered by an electronic device such as a computer 1648. The process can be automated or manually operated.

Figure 17A:
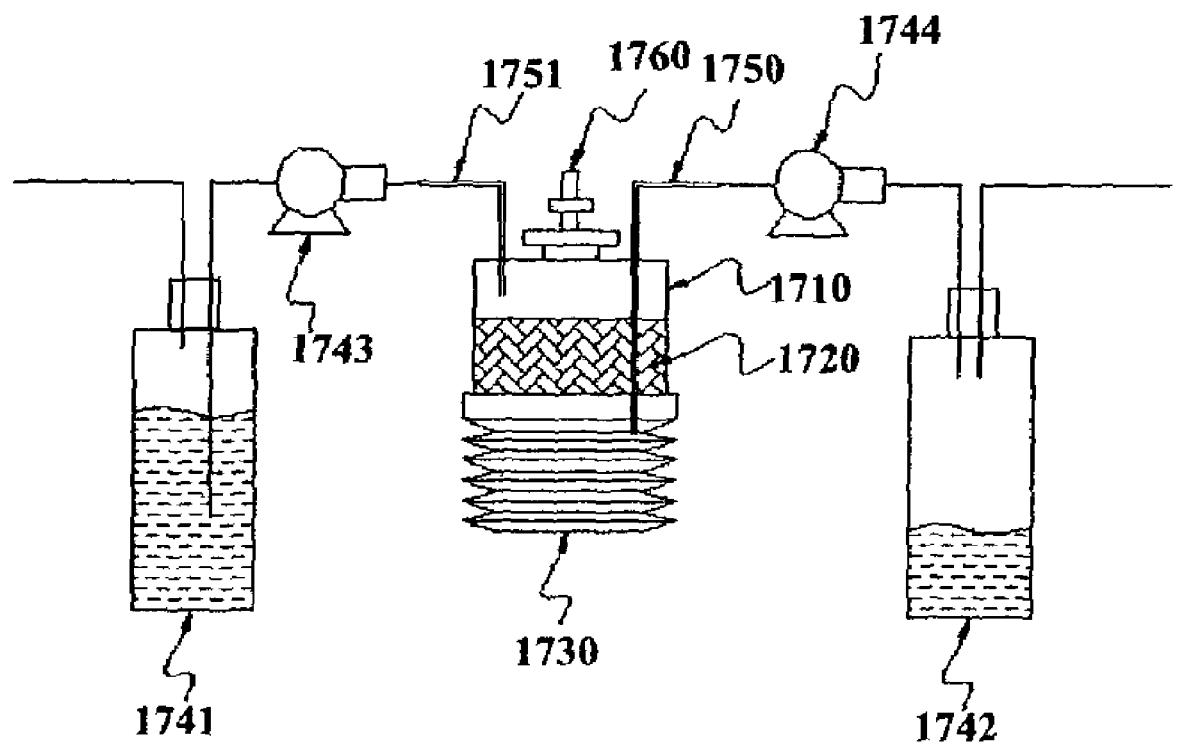
FIG. 17A shows a sixteenth embodiment of the present invention incorporating the cell-cultivating device of the first embodiment and further contains two reservoirs connected to the cell cultivating device in accordance with the present invention in order to replenish fresh culture medium for cultured cells and to collect cellular products dissolved in the spent culture medium contained in the cell cultivating device via pumps.
Figure 17B:
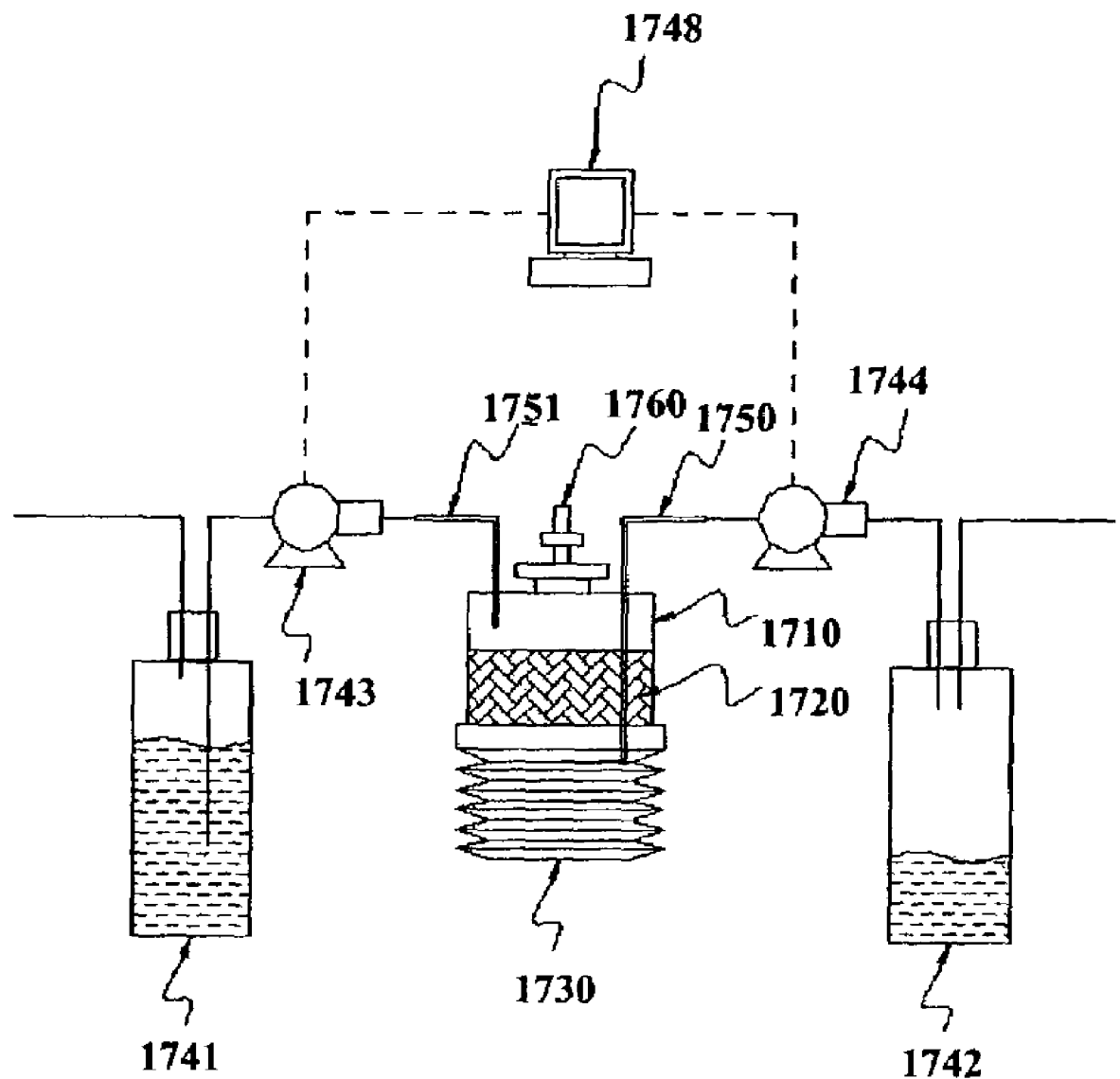
FIG. 17B shows the sixteenth embodiment of the present invention incorporating the cell-cultivating device of the first embodiment and further contains two reservoirs connected to the cell cultivating device in accordance with the present invention in order to replenish fresh culture medium for cultured cells and to collect cellular products dissolved in the spent culture medium contained in the cell cultivating device via pumps optionally controlled by an electronic device system or a computer.

FIGS. 17A and 17B depict a sixteenth embodiment of the present invention. The cell cultivating device depicted in FIG. 1 is shown in cooperation with a medium-exchange system. FIG. 17A shows the sixteenth embodiment operated manually. FIG. 17B shows the sixteenth embodiment operated automatically.

The cell cultivating device is meant to work in two different modes: medium-exchange mode and growth mode. In growth mode, pumps 1743 and 1744 are in an off position. Also, air inlet 1760 is open to allow air exchange with the embodiment as depicted in FIG. 1 previously through air filter 160 (not shown). In this state, fresh growth medium cannot enter nor exit the first and/or second chambers of the cell-cultivating device. Once the medium is spent and/or sufficient secreted protein is produced by the cell culture, the spent medium is harvested to retrieve the protein produced and fresh medium will replace the spent medium collected.

In medium exchange mode, air inlet 1760 can be closed. Pump 1744 is turned on thereby pumping the spent medium of the second chamber 1730 out through the connector tube 1750 and transferred to the storage container 1742. Following release of the spent medium, pump 1744 is turned off. Next, pump 1743 is turned on thereby pumping fresh medium contained in storage container 1741 through the connector tube 1751 to the first chamber 1710 of the cell-cultivating device. Once a sufficient amount of fresh medium has been delivered, pump 1743 is turned off. To reestablish normal growth mode, air inlet 1760 is opened. All pump controls can be powered by computer and/or electronic device 1748. The process can be automated or manually operated.

Figure 18A:
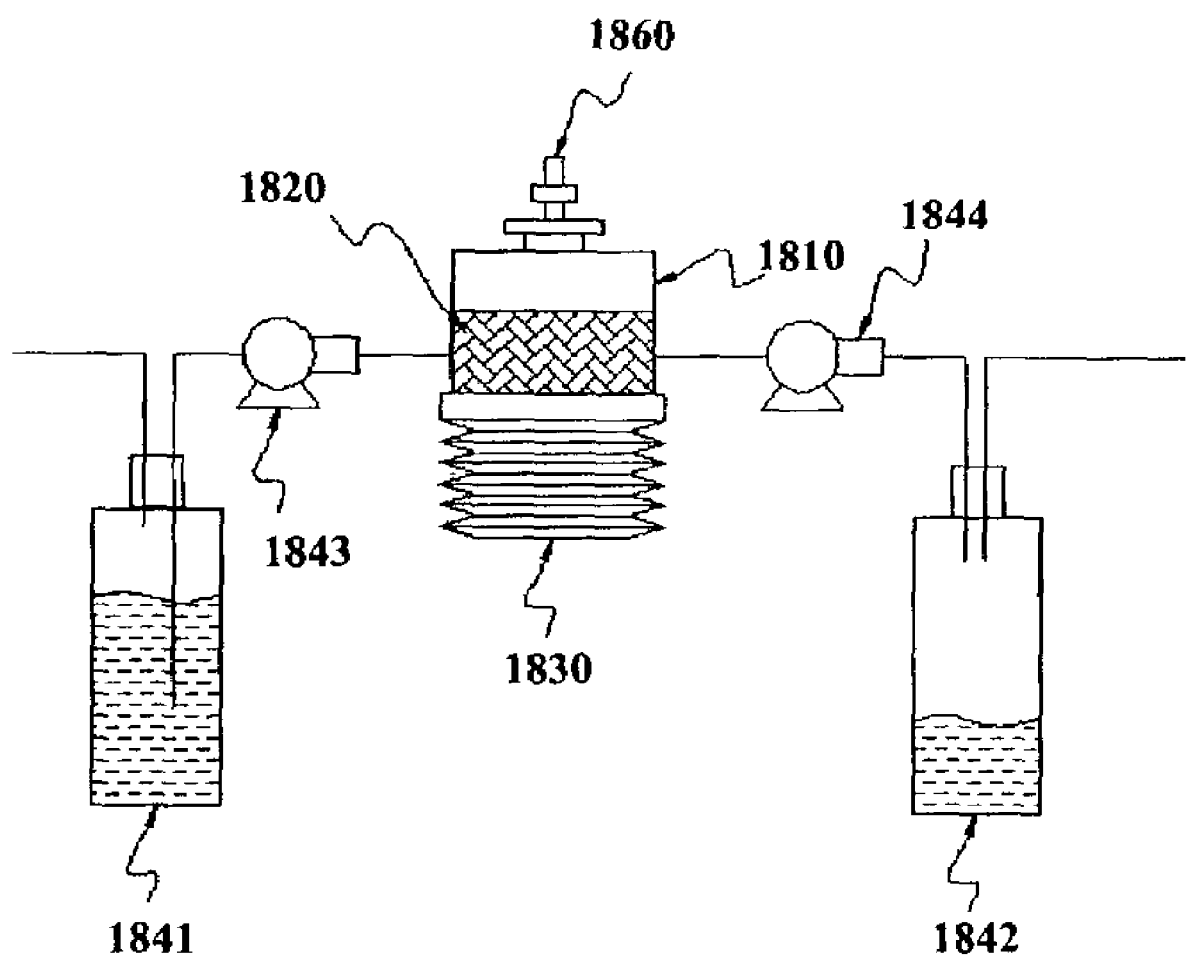
FIG. 18A shows a seventeenth embodiment of the present invention incorporating the cell-cultivating device of the first embodiment and further contains two reservoirs connected to the cell cultivating device in accordance with the present invention in order to replenish fresh culture medium for cultured cells and to collect cellular products dissolved in the spent culture medium contained in the cell cultivating device via pumps.
Figure 18B:
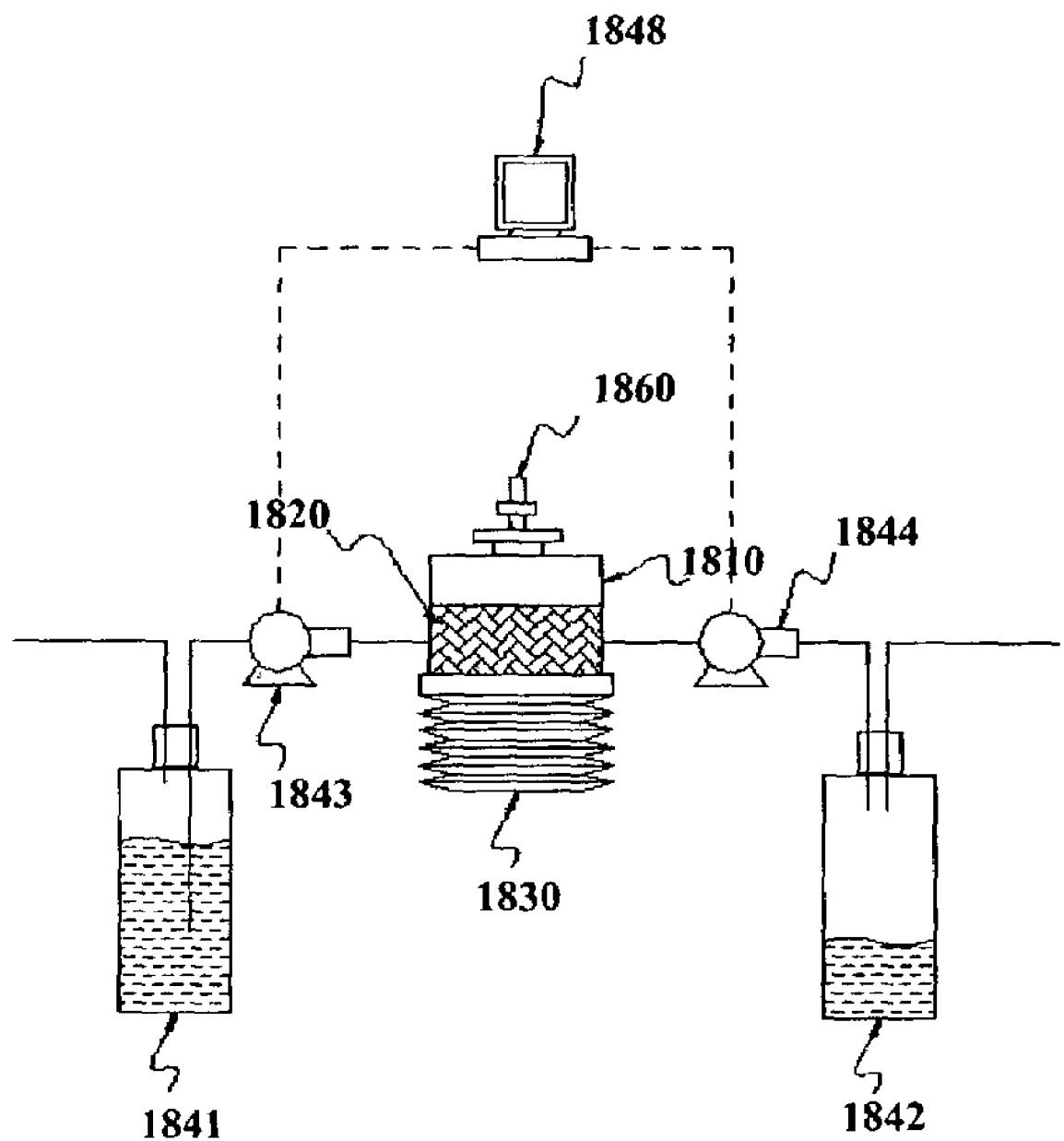
FIG. 18B shows the seventeenth embodiment of the present invention incorporating the cell-cultivating device of the first embodiment and further contains two reservoirs connected to the cell cultivating device in accordance with the present invention in order to replenish fresh culture medium for cultured cells and to collect cellular products dissolved in the spent culture medium contained in the cell cultivating device via pumps controlled by a computer and/or electronic system.

FIGS. 18A and 18B depict a seventeenth embodiment of the present invention. The cell cultivating device depicted in of FIG. 1 is shown in cooperation with a medium-exchange system in accordance with the present invention. FIG. 18A shows the seventeenth embodiment operated manually. FIG. 18B shows the seventeenth embodiment operated automatically.

The medium-exchange system is meant to work in two different modes: medium-exchange mode and growth mode. In growth mode, pumps 1843 and 1844 are in an off position. Also, air inlet 1860 is open to allow air exchange with the cell cultivating device depicted in FIG. 1 through air filter 160 (not shown). In this state, fresh growth medium cannot enter nor exit the first and/or second chambers of the cell-cultivating device. Once the medium is spent and/or contains sufficient secreted protein the spent medium is harvested to retrieve the protein and also to replenish the spent medium with fresh medium.

In medium exchange mode, air inlet 1860 can be closed. Pump 1844 is turned on causing the spent medium to be pumped out of the cell cultivating device through the connector of pump 1844 and into the storage container 1842. Following the collection of the spent medium, pump 1844 is turned off. Pump 1843 is then turned on to replenish the cell-cultivating device with fresh medium contained in container 1841. Once a sufficient amount of fresh medium has been delivered, pump 1843 is turned off. To re-establish normal growth mode, air inlet 1860 is opened. All pump controls can be optionally powered by an electronic device 1848 or a computer. The collection of the spent medium and the refilling of fresh medium can be materialized either automatically or operated manually.

Figure 19A:
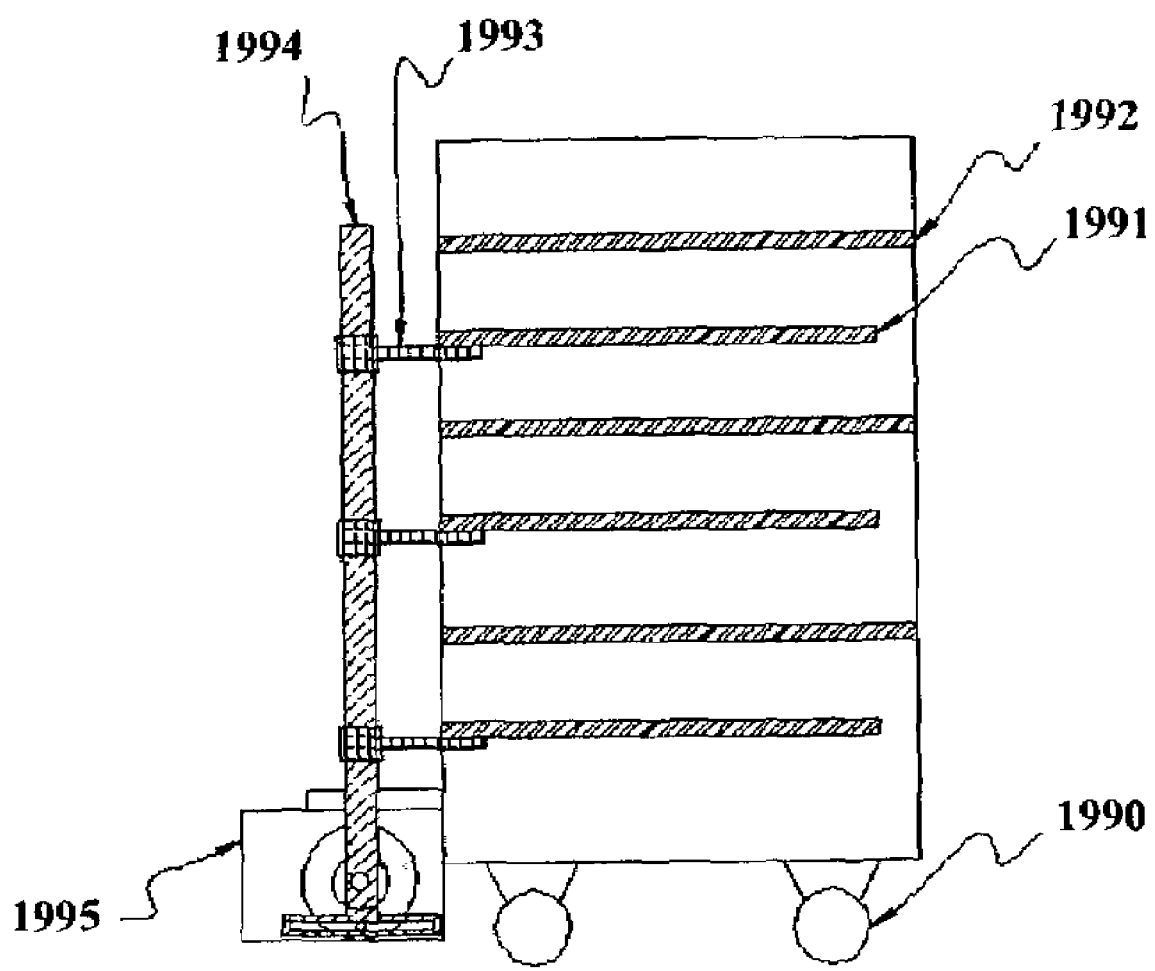
FIG. 19A shows an eighteenth embodiment of the present invention containing at least one growth chamber defining at least one interior open space further containing a movable growth substrate that is connected to a driving means in the form of a lift wherein the growth substrate is submerged in the growth medium.
Figure 19B:
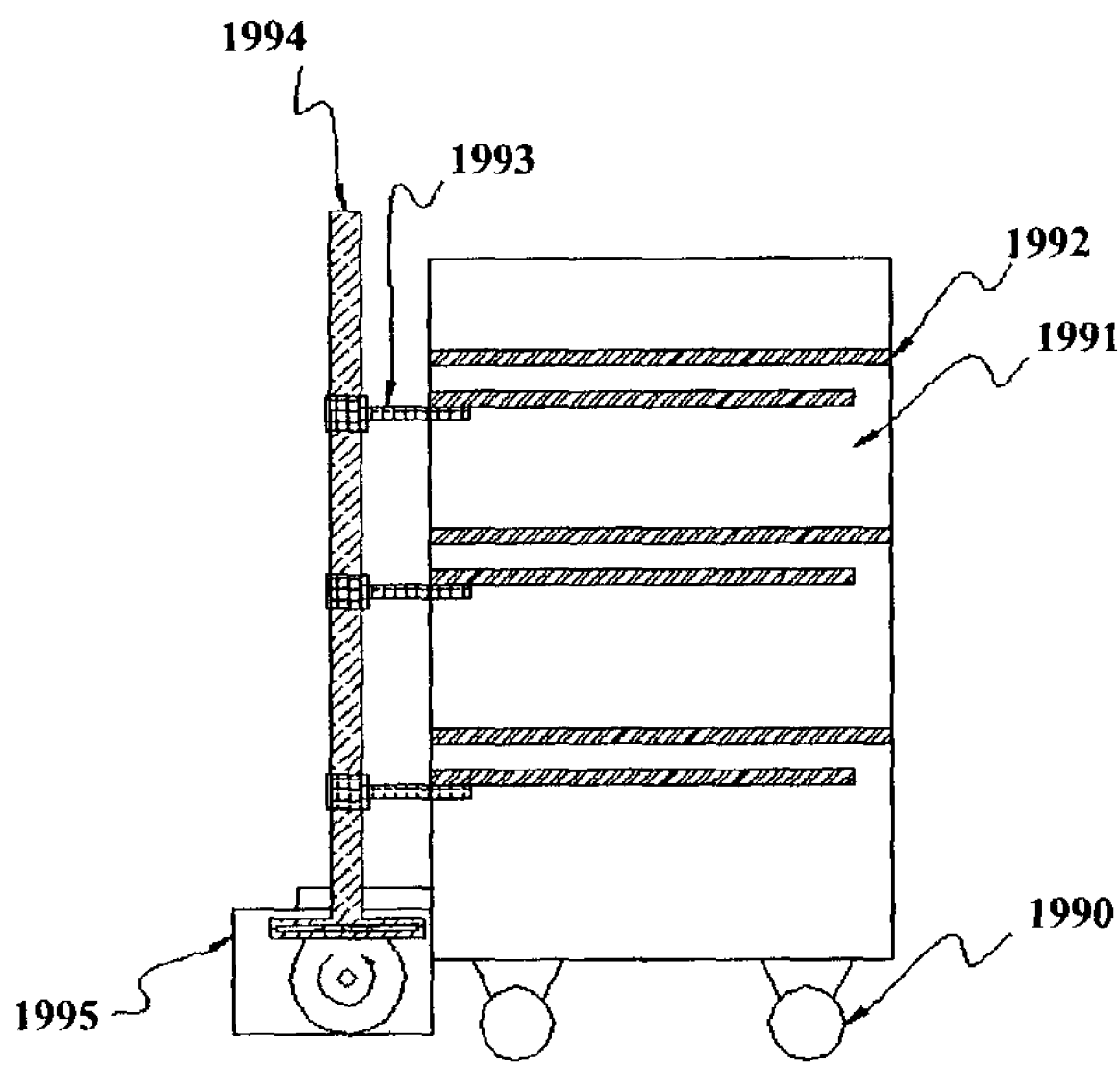
FIG. 19B shows the eighteenth embodiment of the present invention containing at least one growth chamber defining at least one interior open space further containing a movable growth substrate that is connected to a driving means in the form of a lift wherein the growth substrate can freely move in an up and down or left and right direction and is emerged from the growth medium to the growth chamber.

FIGS. 19A and 19B depict an eighteenth embodiment of the present invention. The present embodiment comprises at least one growth chamber, wherein the growth chamber is formed by at least one growth chamber wall 1992 wherein each chamber has a first end, a second end, an interior surface and an exterior surface to define an opening. The cell cultivating device according to the present invention may have a second chamber which is atop, below or side by side with the first growth chamber. At least one growth chamber can be supported on wheels or stands 1990 such that the cell-cultivating device of the present embodiment can be sufficiently supported on a surface, such as a floor, table or a laboratory bench top. Each growth chamber has at least one growth substrate 1991 to receive at least one cell and allow cell anchorage and/or adhesion.

At least one growth chamber is adapted to contain growth medium and a gaseous environment such that the growth medium is substantially contained at the second end of the growth chamber and the gaseous environment is substantially disposed and/or contained in the first end of the growth chamber. The present embodiment also comprises a driving means 1995 for alternately moving growth substrate from the first end to the second end of the growth chamber in an up and down or left and right directions such that the growth substrate is alternately periodically and intermittently submerged in and/or emerged from the growth medium to provide optimal nutrient and oxygen to a cell. The driving means 1995 optionally includes a first connecting means 1994 to join the driving means 1995 with a second connecting means 1993. The driving means 1995 is connected to the growth substrate 1991 to provide a means for alternately, periodically and intermittently, move the growth substrate means from the first end to the second end of the growth chamber, i.e. moving the growth substrate within the growth chamber to alternately be submerged in and emerged from the growth medium in order to provide appropriate nutrient and oxygen to cells. The driving means of the present embodiment can be a lift. The lift mechanism facilitates the movement of the growth substrate means in an up and down or left and right direction.

The growth substrate 1991 of the eighteenth embodiment may optionally be porous. The porous growth substrate means allows the cells contained thereon to be oxygenated without being directly exposed to the shear force of an air stream or air bubbles in the gaseous environment. Direct exposure of the cell to air, particularly animal cells and/or mammalian cells, can be harmful and can lead to cell death and loss of viability of the culture.

The growth substrate means 1991 can be of any form, shape or size including but not limited to a disk, flake, block, plate, sheet, strip, pellet, microcarrier, semi-permeable pellet, macroscopic pellet, semi-permeable membrane, or semi-permeable hollow fiber. Optionally, an envelope of porous membrane can be used to contain the growth substrate means, for example, porous pellets or microcarriers to enable cell culture medium movement. Furthermore, a rigid support structure can also be used to support the growth substrate means to enable the growth substrate means to move in and out of the culture medium.

Figure 20A:
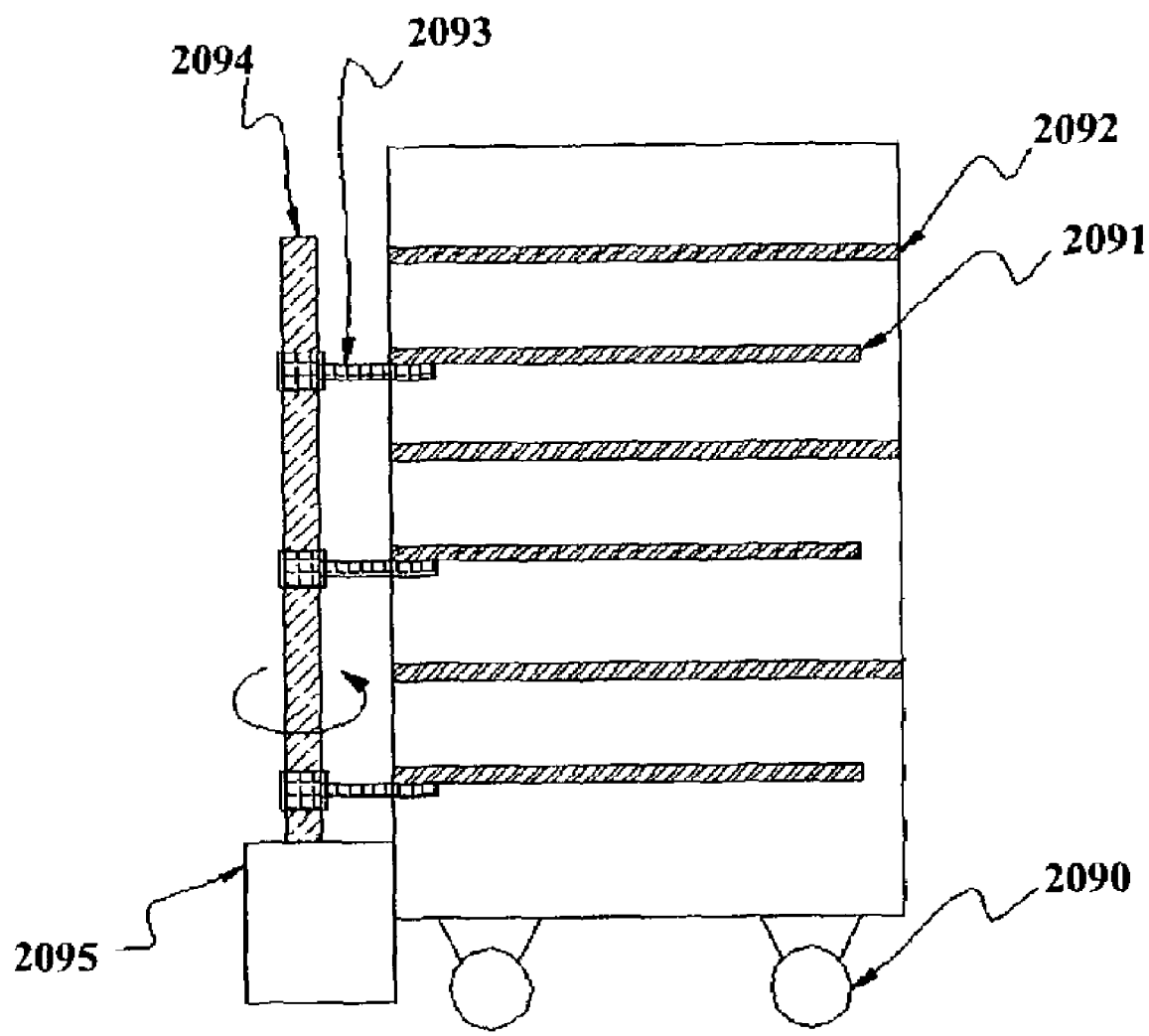
FIG. 20A shows a nineteenth embodiment of the present invention containing at least one growth chamber defining at least one interior open space further containing a movable growth substrate that is connected to a driving means in the form of a screw jack wherein the growth substrate of the growth chamber is submerged in the growth medium.
Figure 20B:
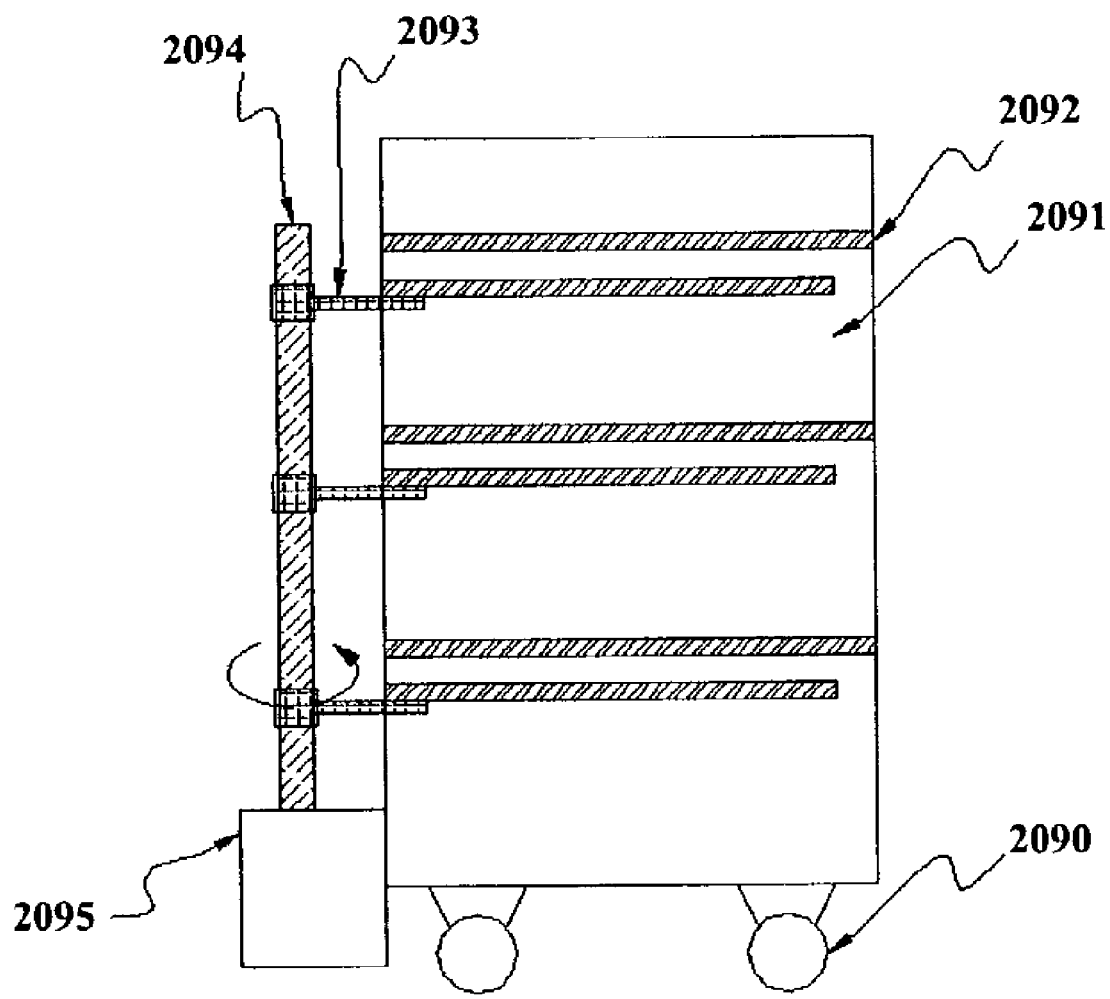
FIG. 20B shows the nineteenth embodiment of the present invention containing at least one separate growth chamber defining at least one interior open space further containing a movable growth substrate that is connected to a driving device in the form of a screw jack wherein the growth substrate of each growth chamber emerged from the growth medium can freely move in an up and down or left and right direction and is to maximize the amount of oxygen in each growth chamber.

FIGS. 20A and 20B depict a nineteenth embodiment of the present invention. The present embodiment comprises a first growth chamber, wherein the growth chamber is formed by at least one growth chamber wall 2092 wherein each chamber has a first end, a second end, an interior surface and an exterior surface to define a opening. The cell cultivating device according to the present invention may have a second growth chamber which is atop, below or side by side with the first growth chamber. At least one growth chamber can be supported on wheels or stands 2090 such that the cell-cultivating device of the present embodiment can sufficiently supported on a surface, such as a floor, table or a laboratory bench top. Each growth chamber has at least one growth substrate 2091 to receive at least one cell and allow cell anchorage and/or adhesion.

At least one growth chamber is adapted to contain growth medium and a gaseous environment such that the growth medium is substantially contained at the second end of the growth chamber and the gaseous environment is substantially disposed and/or contained in the first end of the growth chamber. The present embodiment also comprises a driving means 2095 for alternately moving the growth substrate from the first end to the second end of the growth chamber in an up and down or left and right directions such that the growth substrate is alternately, periodically and intermittently submerged in and/or emerged from the growth medium to provide optimal nutrient and oxygen to a cell. The driving means 2095 optionally includes a first connecting means 2094 to join the driving means 2095 with a connecting means 2093. The driving means 2095 is connected to the growth substrate 2091 to provide a means for alternately, periodically and intermittently move positioning the growth substrate means towards the first end and second end of the growth chamber, i.e. moving the growth substrate within the growth chamber to alternately be submerged in and emerged from the growth medium in order to provide appropriate nutrient and oxygen to cells. The driving means of the present embodiment can be a screw jack mechanism. The screw jack mechanism facilitates the movement of the growth substrate means in an up and down or left and right direction.

The growth substrate 2091 of the nineteenth embodiment may optionally be porous. The porous growth substrate means allows the cells contained thereon to be oxygenated without being directly exposed to the shear force of an air stream or air bubbles in the gaseous environment. Direct exposure of the cell to air, particularly animal cells and/or mammalian cells, can be harmful and can lead to cell death and loss of viability of the culture.

The growth substrate means 2091 can be of any form, shape or size including but not limited to a disk, flake, block, plate, sheet, strip, pellet, microcarrier, semi-permeable pellet, macroscopic pellet, semi-permeable membrane, or semi-permeable hollow fiber. Optionally, an envelope of porous membrane can be used to contain the growth substrate means, for example porous pellets or microcarriers, to enable cell culture medium movement. Furthermore, a rigid support structure can also be used to support the growth substrate means to enable the growth substrate means to move in and out of the culture medium.

While the invention has been described by way of example and in terms of the preferred embodiment, it is to be understood that the invention is not limited to the disclosed embodiments. To the contrary, it is intended to cover various embodiments of the present invention (as would be apparent to those skilled in the art). Therefore, the scope of the appended claims should be accorded the broadest interpretation so as to encompass all such modifications and similar arrangements.

In this disclosure, "comprises", "comprising" and the like can have the meaning ascribed to them in U.S. Patent Law and can mean "includes", "including" and the like.

The invention shall be further described by way of the following non-limiting Examples that are also an illustration of the invention and are not to be considered a limitation of this invention, many apparent variations of which are possible without departing from the spirit or scope thereof.

EXAMPLES

The following example is set forth to illustrate an embodiment in accordance with the present invention, it is by no way limiting nor does this example impose a limitation on the present invention.

Example 1

Cell Culturing and Isolation of Protein Secreted During Growth.

A genetically engineered line of CHO cells, comprising a stably-integrated and expressible DNA encoding a foreign protein of interest will be used to inoculate a semi-permeable microcarrier growth substrate means contained in the cell-culturing device of the present invention. The cell-culturing device according to the present invention comprises two chambers a first chamber and a second chamber. The first chamber atops the second chamber and the first chamber contains a growth substrate means in accordance with the present invention and the second chamber has a compressible bellow and contains culture medium.

Once growth medium and the inoculum are added, the cell-cultivating device will be placed on a driving means to periodically and intermittently compress and decompress the bellow. When the bellow is automatically compressed by the driving means, the growth medium is propelled from the second chamber into the first chamber resulting in the submersion of the microcarrier growth substrate means in the growth medium. When the bellow is decompressed by the driving means, the growth medium travels from the first chamber into the second chamber resulting in the indirect exposure of the microcarrier growth substrate means and the cells contained thereon to the gaseous environment of the first chamber via a thin gas-growth medium interface maintained at the surface of the growth substrate means. The gaseous environment contains an optimal concentration of oxygen.

Further, the microcarrier substrate means will retain a small amount of growth medium on its surface when the growth medium is returned to the second chamber thus protecting the cells from injury caused by an exposure to a gaseous environment. The compression and decompression of the bellow will allow for the periodic and intermittent movement of the growth medium to come into contact with the growth substrate means, and thus, the cells contained thereon to provide the maximum nutrients to the cells. Further, the periodic and intermittent movement of the cells from the second chamber into the first chamber will result in redistribution and reattachment of any dislodged cells thereby increasing the overall viability and productivity of the culture.

The CHO cells, comprising the stably-integrated and expressible DNA encoding the foreign protein of interest, will be grown according to the instant invention, such that optimum cell growth and foreign protein production and secretion is achieved by periodically and intermittently moving the growth medium from one chamber to another chamber in order to alternate nutrient and oxygen supply to cells without ever directly exposing the cells to a gaseous environment. The foreign protein of interest will be secreted into the growth medium and will accumulate in concentration over time.

Once an optimum level of cell growth is achieve, e.g., the growth medium becomes exhausted of all nutrients, the cell growth medium will be removed from the cell-cultivating device and replenished with fresh medium. The cell growth medium will contain the recombinant protein of interest, which ca be purified according to methods well-known in the art.

What is claimed is:

1. A cell-cultivating device, comprising:
    a first chamber having a first end, a second end, an interior surface, and an exterior surface, wherein the interior surface has at least one structure to receive at least one cell and allow cell anchorage and/or adhesion, and wherein a gaseous environment is disposed within the first chamber;
    a second chamber connected to the second end of the first chamber, the second chamber having a first end, a second end, an interior surface, and an exterior surface, the second chamber being a compressible body; and
    communicating means disposed between the second end of the first chamber and the first end of the second chamber;

wherein culture medium is disposed within the second chamber, the culture medium being movable between the first and the second chambers through the communicating means when the second chamber is compressed and decompressed, such that when the second chamber is compressed the structure where at least one cell is anchored and/or adhered is submerged by the culture medium, and when the second chamber is decompressed the structure where at least one cell is anchored and/or adhered emerges from the culture medium and is indirectly exposed to the gaseous environment of the first chamber through a thin gas-growth medium interface to provide oxygenation.

2. The cell-cultivating device of claim 1, further comprising driving means for compressing and decompressing the second chamber to move the culture medium between the first and second chambers, such that the structure is submerged in the cultured medium when the second chamber is compressed to a first level, and the structure is emerged from the culture medium when the second chamber is decompressed to a second level.

3. The cell-cultivating device of claim 1, wherein the first chamber further comprises at least one opening, wherein the at least one opening is adapted to receive and remove the culture medium for plating the at least one cell and allows for the exchange of air between the cell-cultivating device and an environment external to the cell-cultivating device.

4. The cell-cultivating device of claim 3, wherein the opening in the first chamber is adapted to receive a closing means.

5. The cell-cultivating device of claim 4, wherein the closing means is fitted with an air filter to prevent contamination.

6. The cell-cultivating device of claim 2, wherein the driving means is automated or manual.

7. The cell-cultivating device of claim 1, wherein the communicating means is a permeable membrane, wherein the culture medium can travel through the permeable membrane from the second chamber to the first chamber and vice versa.

8. The cell-cultivating device of claim 7, wherein the permeable membrane is porous.

9. The cell-cultivating device of claim 1, wherein the structure is a porous growth substrate means.

10. The cell-cultivating device of claim 9, wherein the porous growth substrate means is a loosely-packed matrix that provides a large surface area for cell attachment and/or adhesion, and functions as a depth filter, an oxygenator, and a static mixer.

11. The cell-cultivating device of claim 1, wherein the at least one cell is selected from the group consisting of eukaryotic cells, prokaryotic cells, mammalian cells, animal cells, human cells, bacterial cells, and fungal cells.

12. The cell-cultivating device of claim 1, wherein the cell-cultivating device is adapted for growing three-dimensional tissue culture.

13. The cell-cultivating device of claim 2, wherein the driving means is a screw jack.

14. The cell-cultivating device of claim 2, wherein the structure is a porous growth substrate means and the at least one cell is embedded in the porous growth substrate means, such that when the porous growth substrate means emerges from the culture medium the at least one cell embedded in the porous growth substrate means receives oxygenation through the thin gas-growth medium interface without directly coming into contact with the gaseous environment.

15. The cell-cultivating device of claim 14, wherein the porous growth substrate means is made from a material selected from the group consisting of ceramics, polymers, woven substrates, non-woven substrates, polyamide, polyester, polyurethane, fluorocarbon polymers, polyethylene, polypropylene, and polyvinyl alcohol.

* * * * *